(12) United States Patent
Li

(10) Patent No.: US 7,087,622 B2
(45) Date of Patent: Aug. 8, 2006

(54) PYRIDONE COMPOUNDS AS INHIBITORS OF BACTERIAL TYPE III PROTEIN SECREATION SYSTEMS

(75) Inventor: Xiaobing Li, Flemington, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/123,995

(22) Filed: May 6, 2005

(65) Prior Publication Data

US 2005/0256137 A1 Nov. 17, 2005

Related U.S. Application Data

(60) Provisional application No. 60/568,855, filed on May 7, 2004.

(51) Int. Cl.
*C07D 211/84* (2006.01)
*A61K 31/44* (2006.01)
(52) U.S. Cl. ..................... 514/319; 546/297
(58) Field of Classification Search ........... 514/349; 546/297
See application file for complete search history.

(56) References Cited

FOREIGN PATENT DOCUMENTS

| WO | WO 98/13043 | 4/1998 |
|---|---|---|
| WO | WO 99/26926 | 6/1999 |
| WO | WO 01/40189 | 6/2001 |
| WO | WO 03/103668 | 12/2003 |

OTHER PUBLICATIONS

Dragovich, P.S. et al., "Structure-Based Design, Synthesis and Biological Evaluatin of Irreversible Human Rhinovirus 3C Protease Inhibitors. 6. Structure-Activity Studies of Orally Bioavailable, 2-Pyridone-Cntaining Peptidomimetics", J. Med. Chem vol. 45, 2002, pp. 1607-1623.
PCT International Search Report, dated Oct. 5, 2005, for PCT Int'l. Appln. No. PCT/US2005/015811.

*Primary Examiner*—Zinna N. Davis
(74) *Attorney, Agent, or Firm*—Thomas Dodd

(57) ABSTRACT

In accordance with the present invention, compounds that inhibit Type III protein section have been identified, and methods for their use provided. In one aspect of the invention, compounds useful in the inhibition of Type III protein section and/or in the treatment and prevention of bacterial infections, particularly Gram-negative bacterial infections, are provided. In another aspect of the invention, methods are provided for the inhibition of Type III protein secretion and/or the treatment and prevention of bacterial infections, particularly Gram-negative bacterial infections using the compounds of the invention.

12 Claims, No Drawings

PYRIDONE COMPOUNDS AS INHIBITORS OF BACTERIAL TYPE III PROTEIN SECRETION SYSTEMS

CROSS-REFERENCE TO RELATED APPLICATIONS

This applications claims the benefit under 35 U.S.C. 119(e) of provisional application Ser. No. 60/568,855, filed May 7, 2004.

FIELD OF THE INVENTION

The subject invention relates to novel pyridone compounds that have anti-microbial activity, their compositions and their uses.

BACKGROUND OF THE INVENTION

Type III protein secretion systems are an essential virulence determinant of most pathogenic Gram-negative bacteria, including *Salmonella, Shigella, Yersinia, Pseudomonas aeruginosa*, and enteropathogenic *Escherichia coli*. The Type III virulence mechanism consists of a secretion apparatus, consisting of about 25 proteins, and a set of effector proteins released by this apparatus. Following activation by intimate contact with a eukaryotic cell membrane, the effector proteins are injected into the host cell, where they subvert the signal transduction machinery and lead to a variety of host cell responses. This virulence mechanism plays a key role in establishing and maintaining an infection and in the resulting pathophysiological sequelae, such as diarrhea, chronic lung inflammation, and septicemia.

Certain protein components of the Type III secretion apparatus are highly conserved among bacterial pathogens, and as such represent suitable targets for therapeutic intervention. Inhibitors of Type III protein secretion are expected to be useful as prophylactic agents (i.e., to prevent the onset of infection by Gram-negative bacteria) or as drugs to treat an existing bacterial infection, either with or without an anti-bacterial agent.

There remains a need to develop, characterize, and optimize lead molecules for the development of novel anti-bacterial drugs.

SUMMARY OF THE INVENTION

In accordance with the present invention, compounds that inhibit Type III protein secretion have been identified, and methods for their use provided.

In one aspect of the invention, compounds of Formula (I) are provided which are useful in the inhibition of Type III protein secretion and/or in the treatment and prevention of bacterial infection, particularly Gram-negative bacterial infection.

In another aspect of the invention, methods are provided for the inhibition of Type III protein secretion and/or in the treatment and prevention of bacterial infection, particularly Gram-negative bacterial infection using the compounds described herein.

In one embodiment, the invention is directed to methods for inhibiting Type III protein secretion comprising administering a secretion-inhibiting amount of at least one compound of the invention to a subject in need thereof.

In another embodiment, methods for treating and/or preventing bacterial infection, particularly Gram-negative bacterial infection, are provided comprising administering a therapeutically or prophylactically effective amount of at least one compound of the invention to a subject in need thereof.

These and other aspects of the invention will be more clearly understood with reference to the following preferred embodiments and detailed description.

DETAILED DESCRIPTION OF THE INVENTION

Inhibition of Type III protein secretion is an important factor in the treatment and prevention of bacterial infection. In accordance with the present invention, compounds that inhibit Type III protein secretion have been identified, and methods for their use provided.

A. Compounds of the Invention

In one aspect of the invention, compounds of the invention are provided which are useful in the inhibition of Gram-negative bacterial Type III protein secretion systems, and/or in the treatment or prevention of bacterial infection, particularly Gram-negative bacterial infection.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to a mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

Certain of the compounds of the invention, for example the imidazole derivatives, may exist as tautomers. It is understood that such tautomeric forms are intended to be encompassed within the scope of the invention.

As used herein, "enantiomerically pure" refers to compositions consisting substantially of a single isomer, preferably consisting of 90%, 92%, 95%, 98%, 99%, or 100% of a single isomer.

Included within the scope of the invention are the hydrated forms of the compounds that contain various amounts of water, for instance, the hydrate, hemihydrate, and sesquihydrate forms. The present invention also includes within its scope prodrugs and pharmaceutically acceptable salts of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Preferred compounds of the present invention useful in the inhibition of Type III protein secretion include those of Formula (I) as shown below.

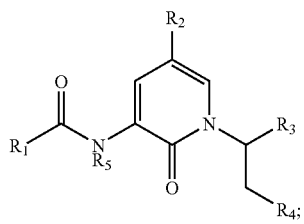

(I)

wherein $R_1$ is aryl or substituted aryl;
$R_2$ is aryl-($C_2$–$C_4$ alkynyl)-; aryl, substituted aryl, or heteroaryl optionally substituted by acyl;
$R_3$ is hydrogen or carboxy;
$R_4$ is aryl, substituted aryl, benzylthio, or benzyloxy;
$R_5$ is hydrogen or lower alkyl;
or an optical isomer, diastereomer or enantiomer thereof; or a pharmaceutically acceptable salt, hydrate, ester or prodrug thereof.
acceptable salt, hydrate, or prodrug thereof.

Certain preferred compounds of Formula I include the following.

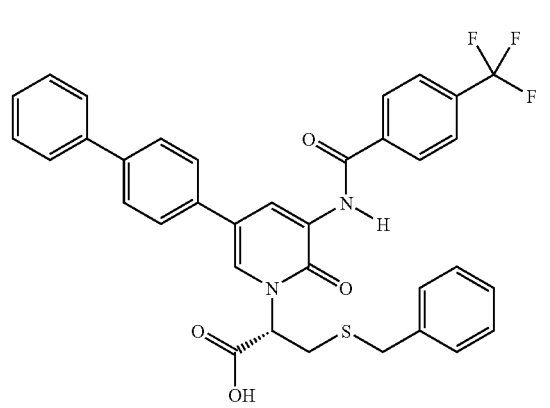

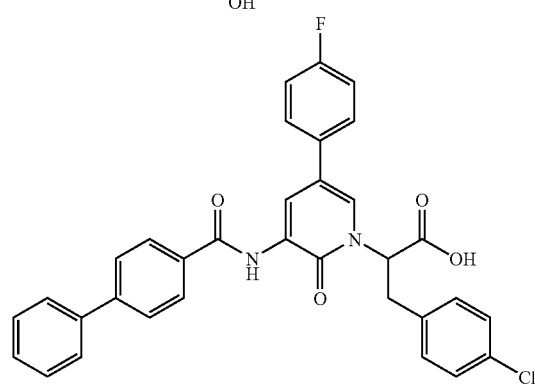

-continued

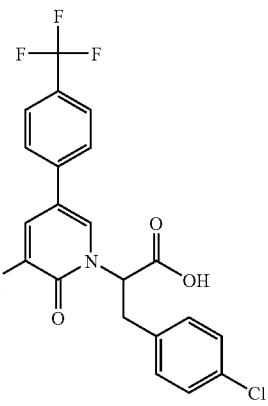

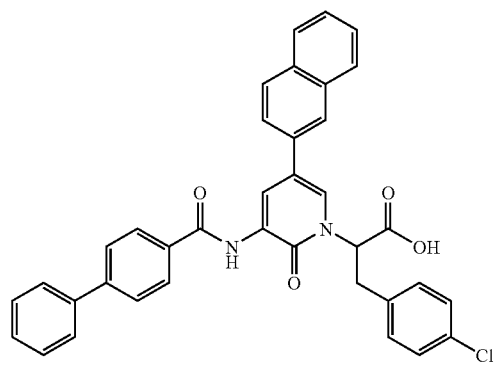

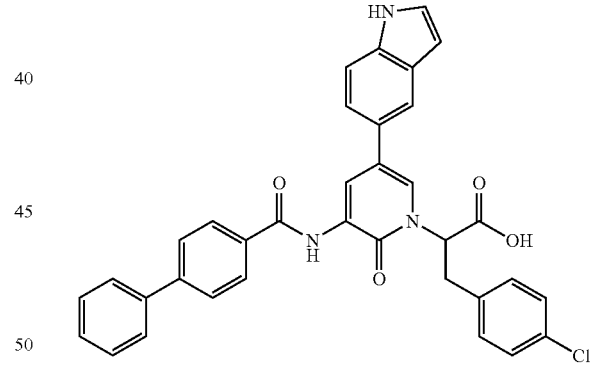

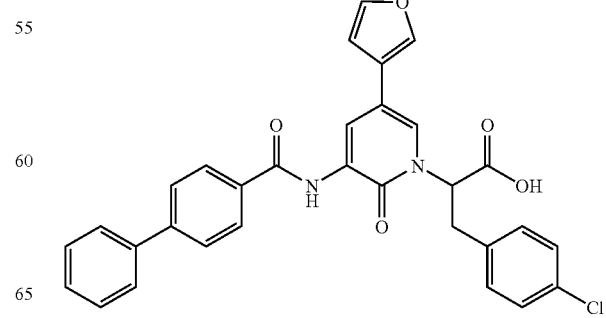

-continued

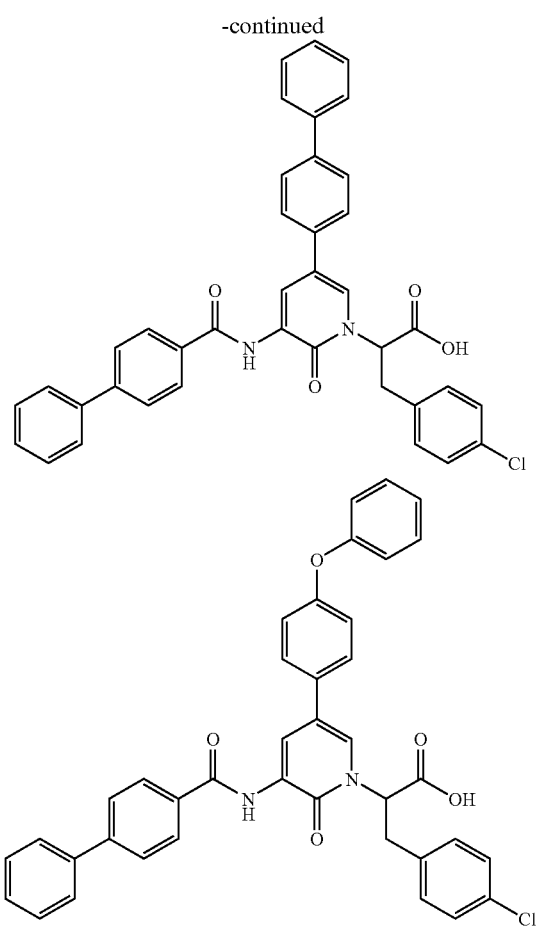

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl," "alkenyl," and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon-carbon double bond. "Alkynyl" refers to a straight or branched chain hydrocarbon with at least one carbon-carbon triple bond. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl.

"Alkoxy" radicals are oxygen ethers formed from the previously described straight or branched chain alkyl groups.

"Cycloalkyl" groups contain 3 to 8 ring carbons and preferably 5 to 7 ring carbons.

The alkyl, alkenyl, alkynyl, cycloalkyl groups and alkoxy groups may be independently substituted with one or more members of the group including, but not limited to, halogen, alkyl, alkenyl, alkynyl, cycloalkyl, oxo, aryl, heteroaryl, heterocyclo, CN, nitro, —OCOR$_5$, —OR$_5$, —SR$_5$, —SOR$_5$, —SO$_2$R$_5$, —COOR$_5$, —NR$_5$R$_6$, —CONR$_5$R$_6$, —OCONR$_5$R$_6$, —NHCOR$_5$, —NHCOOR$_5$, —NHC(NH)NHNO$_2$, and —NHCONR$_5$R$_6$, wherein R$_5$ and R$_6$ are independently selected from hydrogen, alkyl, alkenyl, alkynyl, cycloalkyl, aryl, heteroaryl, heterocyclo, aralkyl, heteroaralkyl, and heterocycloalkyl, or alternatively R$_5$ and R$_6$ may join to form a heterocyclic ring containing the nitrogen atom to which they are attached.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo or iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with aryl, heteroaryl, halogen, OH, CN, mercapto, nitro, amino, $C_1$–$C_8$-alkyl, $C_2$–$C_8$-alkenyl, $C_1$–$C_8$-alkoxy, $C_1$–$C_8$-alkylthio, $C_1$–$C_8$-alkyl-amino, di($C_1$–$C_8$-alkyl) amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl. "Bz" denotes benzoyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrrolyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzisothiazolyl, benzisoxazolyl, benzodiazinyl, benzofurazanyl, indazolyl, indolizinyl, benzofuryl, cinnolinyl, quinoxalinyl, pyrrolopyridinyl, furopyridinyl (such as furo[2,3-c]pyridinyl, furo[3,2-b]pyridinyl, or furo[2,3-b]pyridinyl), imidazo-pyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with aryl, heteroaryl, halogen, OH, CN, mercapto, nitro, amino, $C_1$–$C_8$-alkyl, $C_1$–$C_8$-alkoxy, $C_1$–$C_8$-alkylthio, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully saturated, partially saturated, or non-aromatic cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom. The heterocyclic group may be substituted by independent replacement of 1 to 3 of the hydrogen atoms thereon with aryl, heteroaryl, halogen, $C_1$–$C_8$-alkyl, $C_1$–$C_8$-alkoxy, carboxy, alkoxycarbonyl, or carboxamide.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzothiopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like.

Substituted aryl, substituted heteroaryl, and substituted heterocycle may also be substituted with a second substituted aryl, a second substituted heteroaryl, or a second substituted heterocycle to give, for example, a 4-pyrazol-1-yl-phenyl or 4-pyridin-2-yl-phenyl.

The term "carbocyclic" refers to a saturated or unsaturated, non-aromatic, monocyclic, hydrocarbon ring of 3 to 7 carbon atoms.

Designated numbers of carbon atoms (e.g., $C_1$–$C_8$ or $C_{1-8}$) shall refer independently to the number of carbon atoms in an alkyl or cycloalkyl moiety or to the alkyl portion of a larger substituent in which alkyl appears as its prefix root.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; pivaloyl; phenylsulfonyl; triphenylmethyl; trisubstituted silyl such as trimethylsilyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl; acyl and aroyl such as acetyl, benzoyl, pivaloylbenzoyl, 4-methoxybenzoyl, 4-nitrobenzoyl and phenylacetyl.

The phrase "a pharmaceutically acceptable salt" denotes one or more salts of the free base or free acid which possess the desired pharmacological activity of the free base or free acid as appropriate and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, benzenesulfonic acid, salicylic acid and the like. Suitable salts are furthermore those of inorganic or organic bases, such as KOH, NaOH, $Ca(OH)_2$, $Al(OH)_3$, piperidine, morpholine, ethylamine, triethylamine and the like.

The term "subject" includes, without limitation, any animal or artificially modified animal. As a particular embodiment, the subject is a human.

The term "drug-resistant" or "drug-resistance" refers to the characteristics of a microbe to survive in the presence of a currently available antimicrobial agent such as an antibiotic at its routine, effective concentration.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Further, where a more generic substituent is set forth for any position in the molecules of the present invention, it is understood that the generic substituent may be replaced with more specific substituents, and the resulting molecules are within the scope of the molecules of the present invention.

B. Preparation of Compounds of the Invention

Compounds of the invention may be produced in any manner known in the art. By way of example, compounds of the invention may be prepared according to the following general schemes. The skilled artisan will also recognize the judicious choice of reactions, solvents, and temperatures are an important component in successful synthesis. While the determination of optimal conditions, etc. is routine, it will be understood that a variety of compounds can be generated in a similar fashion, using the guidance of the schemes below.

The starting materials used in preparing the compounds of the invention are known, made by published synthetic methods or available from commercial vendors.

It is recognized that the skilled artisan in the art of organic chemistry can readily carry out standard manipulations of the organic compounds without further direction; that is, it is well within the scope and practice of the skilled artisan to carry out such manipulations. These include, but are not limited to, reductions of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Feiser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. Examples of these manipulations can be found for example in T. Greene, *Protecting Groups in Organic Synthesis*.

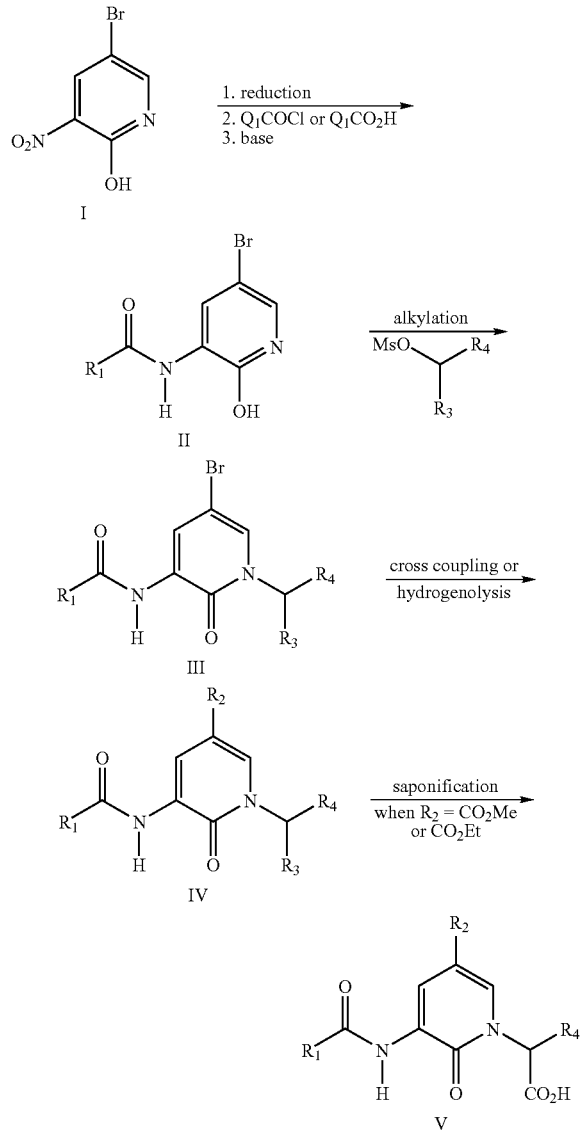

Pyridones (V) of Formula 1 can be prepared by the method outlined in Scheme 1. Reduction of the nitro group of commercially available 2-hydroxy-3-nitro-5-bromo-pyridine (I) can be accomplished by treatment with tin chloride in ethanol or ethyl acetate, or alternatively zinc or iron powder in acetic acid, for from 1 to 48 hours at a temperature ranging from 0° C. to 120° C., to give the corresponding 3-amino pyridine derivative. Reaction of a suitably substituted acid chloride with the 3-amino pyridine derivative, in the presence of a tertiary amine base, such as DBU, triethylamine, diisopropylethylamine, or the like, in an inert solvent, such as methylene chloride, chloroform, tetrahydrofuran or acetonitrile, for from 1 to 48 hours at a temperature ranging from −20° C. to 37° C., affords the corresponding N- and O-diacylated derivative, which can be converted to mono acylated pyridine derivative (II) by reaction with a nucleophilic base, such as potassium carbonate or sodium carbonate, in a suitable solvent, such as tetrahydrofuran, ethanol or methanol, for from 1 to 48 hours at a temperature ranging from −20° C. to 37° C. N-alkylation of (II) can be carried out by reaction of a suitably substituted methanesulfonate, in the presence of a base, such as sodium hydride, potassium hydride, lithium bis(trimethylsilyl)amide, sodium bis(trimethylsilyl)amide, or the like, in an inert solvent, such as tetrahydrofuran, diethyl ether or dioxane, for from 1 to 48 hours at a temperature ranging from −20° C. to 80° C. Reaction at the C-5 position of pyridone derivative (III) can be achieved by one of the following methods:

1) a palladium-catalyzed Suzuki coupling reaction, with a suitably substituted boronic acid, catalyzed by, for example, bis(dibenzylideneacetone)palladium(0) (Pd (dba)$_2$), bis(tri-tert-butylphosphine) palladium(0) (Pd (P$^t$Bu$_3$)$_2$), or dichloro bis(triphenylphosphine) palladium(II) ((PPh$_3$)$_2$PdCl$_2$), using tris(o-furyl)phosphine (TFP), triphenylphosphine (TPP) or 1,1'-bis(diphenylphosphino)-ferrocene (dppf) as ligand, in the presence of a base, such as, triethylamine or cesium fluoride;

2) a Heck-type or a Sonogashira-type cross-coupling reaction, catalyzed by, for example, palladium acetate, with an aryl alkene or aryl alkyne, respectively, using, for example, triphenylphosphine as ligand and triethylamine as base, optionally in the presence of copper (I) iodide; and 3) in the case where Q$_2$ is hydrogen, the bromide of III may be replaced with hydrogen by reaction with hydrogen gas in the presence of a catalyst, such as palladium on carbon.

Removal of the ester protecting group of (IV) by saponification with an alkali metal hydroxide, such as lithium hydroxide, sodium hydroxide or potassium hydroxide, in a suitable solvent, such as tetrahydrofuran, tetrahydrofuran/water mixture, ethanol, methanol, water, or an alcohol/water mixture, at a temperature ranging from 0° C. to 80° C. for from 1 to 48 hours, provides the corresponding acid derivative (V).

The following examples describe in detail the chemical synthesis of representative compounds of the present invention. The procedures are illustrations, and the invention should not be construed as being limited by the chemical reactions and conditions they express. No attempt has been made to optimize the yields obtained in these reactions, and it would be obvious to one skilled in the art that variations in reaction times, temperatures, solvents, and/or reagents could increase the yields.

In certain preferred embodiments, compounds of the invention may be resolved to enantiomerically pure compositions or synthesized as enantiomerically pure compositions using any method known in art. By way of example, compounds of the invention may be resolved by direct crystallization of enantiomer mixtures, by diastereomer salt formation of enantiomers, by the formation and separation of diastereomers or by enzymatic resolution of a racemic mixture.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the inhibition of Type III protein section, and/or the treatment and prevention of bacterial infection, particularly Gram-negative bacterial infection using the compounds described herein.

In one embodiment, the invention is directed to methods for inhibiting Type III protein secretion comprising administering a secretion-inhibiting amount of at least one compound of the invention to a subject in need thereof.

In yet another embodiment, methods for treating or prevention bacterial infection, particularly Gram-Negative bacterial infection are provided comprising administering a therapeutically or prophylactically effective amount of at least one compound of the invention to a subject in need thereof.

According to the methods of the invention, the compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "secretion-inhibiting amount", "therapeutically effective amount", and "prophylactically effective amount", as used herein, refer to an amount of a compound of the invention sufficient to treat, ameliorate, or prevent the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 μg/mL to approximately 100 μg/mL, preferably from approximately 10 μg/mL to approximately 100 μg/mL, more preferably from approximately 20 μg/mL to approximately 100 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment or prevention of bacterial infection (e.g., anti-bacterial or anti-microbial agents).

Formulations of the present invention, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-α-cyclodextrin, and even more preferably from 2.5% to 10% hydroxypropyl-α-cyclodextrin. The amount of solubility enhancer employed will depend on the amount of the compound of the present invention in the composition.

F. Combination Therapy

It is also possible to combine any compound of the present invention with one or more other active ingredients useful in the treatment or prevention of bacterial infection, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the Type III protein secretion-inhibiting activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

The following examples describe in detail the chemical synthesis of representative compounds of the present invention. The procedures are illustrations, and the invention should not be construed as being limited by the chemical reactions and conditions they express. No attempt has been made to optimize the yields obtained in these reactions, and it would be obvious to one skilled in the art that variations in reaction times, temperatures, solvents, and/or reagents could increase the yields.

Example 1

Preparation of Compounds of the Invention

Compounds of Formula I may be prepared according to the schemes disclosed herein as follows.

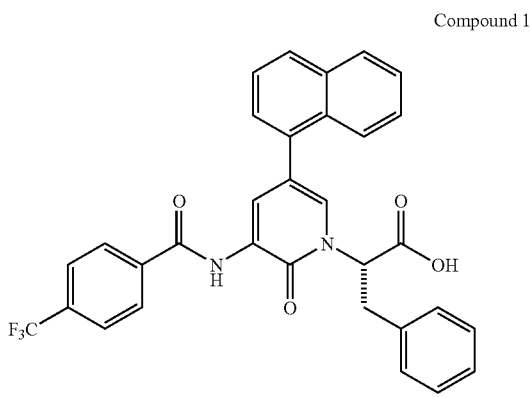

Compound 1

(S)-2-[5-Naphthalen-1-yl-2-oxo-3-(4-trifluoromethylbenzoylamino)-2H-pyridin-1-yl]-3-phenylpropionic acid

Step A: (R)-2-Hydroxy-3-phenylpropionic acid methyl ester

To a solution of (R)-2-hydroxy-3-phenylpropionic acid (1.5 g, 12.9 mol) in methanol (18 mL) at 0° C. was added concentrated sulfuric acid (0.2 mL). The reaction mixture was stirred at 0° C. for 30 min and warmed to room temperature for 24 h. Concentration in vacuo gave a residue which was diluted with diethyl ether (200 mL) and washed with water, saturated sodium bicarbonate and brine. The organic layer was separated, dried with sodium sulfate, filtered and concentrated in vacuo giving a white solid 1.62 g (85%), which was used without further purification.

Step B: (R)-2-Methanesulfonyloxy-3-phenylpropionic acid methyl ester

To a solution of (R)-2-hydroxy-3-phenylpropionic acid methyl ester from Step A (1.62 g, 10.9 mol) and triethylamine (3.0 mL, 21.8 mol) in dichloromethane (21.8 mL) at 0° C. was added dropwise methanesulfonyl chloride (1.28 mL, 16.4 mol). The reaction mixture was stirred at 0° C. for 1 h and was diluted with diethyl ether (200 mL) and washed with saturated ammonium chloride solution and brine. The organic layer was separated, dried with magnesium sulfate, filtered and concentrated in vacuo to give a light yellow solid 2.43 g (73%), which was used without further purification.

Step C: 3-Amino-5-bromopyridin-2-ol

A mixture of 5-bromo-3-nitropyridin-2-ol (1.26 g, 4.6 mmol) and tin chloride dihydrate (3.91 g, 17.3 mmol) in ethyl acetate (19.3 mL) was heated at 50° C. for 20 h. The reaction mixture was cooled to room temperature and diluted with ethyl acetate (100 mL) and washed with brine. The aqueous layer was separated and extracted with ethyl acetate (5×50 mL). The combined organic layers were dried with sodium sulfate, filtered and concentrated in vacuo to give a black solid 580 mg (53%), which was used without further purification.

Step D: N-(5-Bromo-2-hydroxypyridin-3-yl)-4-trifluoromethylbenzamide

To a solution of 3-amino-5-bromopyridin-2-ol from Step C (1.5 g, 7.9 mol) and triethylamine (1.64 mL, 11.9 mol) in tetrahydrofuran (15.8 mL) at 0 C was added dropwise 4-trifluoromethylbenzoyl chloride (1.2 mL, 7.9 mol). The reaction mixture was stirred at 0° C. for 1 h and warmed to room temperature for 15 h. Potassium carbonate (1.64 g, 11.9 mol) and methanol (15.8 mL) were added and the reaction mixture was stirred at room temperature for 6 h. The reaction mixture was diluted with ethyl acetate (100 mL) and washed with saturated ammonium chloride solution and brine. The separated organic layer was dried with sodium sulfate, filtered and concentrated in vacuo. Purification by medium pressure liquid chromatography on silica gel (1:5 ethyl acetate/hexanes) gave 1.72 g (60%) of the title compound.

Step E: (S)-2-[5-Bromo-2-oxo-3-(4-trifluoromethylbenzoylamino)-2H-pyridin-1-yl]-3-phenylpropionic acid methyl ester To a solution of N-(5-bromo-2-hydroxypyridin-3-yl)-4-trifluoromethyl-benzamide from Step D (760 mg, 2.1 mmol) in tetrahydrofuran (10 mL) was added 95% sodium hydride (80 mg, 3.15 mmol) at room temperature. After the reaction mixture was stirred at room temperature for 30 min, (R)-2-methanesulfonyloxy-3-phenylpropionic acid methyl ester from Step B (820 mg, 3.15 mmol) was added and the reaction was stirred and heated at 50° C. for 20 h. The reaction mixture was cooled to room temperature and diluted with ethyl acetate (100 mL) and washed with saturated ammonium chloride solution and brine. The organic layer was separated, dried with sodium sulfate, filtered and concentrated in vacuo. Purification by medium pressure liquid chromatography on silica gel (1:6 ethyl acetate/hexanes) gave 770 mg (70%) of the title compound as a semisolid.

Step F: (S)-2-[5-Naphthalen-1-yl-2-oxo-3-(4-trifluoromethylbenzoylamino)-2H-pyridin-1-yl]-3-phenylpropionic acid methyl ester A mixture of (S)-2-[5-bromo-2-oxo-3-(4-trifluoromethylbenzoylamino)-2H-pyridin-1-yl]-3-phenylpropionic acid methyl ester from Step E (66.8 mg, 0.128 mmol), 1-naphthyleneboronic acid (44.0 mg, 0.256 mmol), cesium fluoride (97 mg, 0.64 mmol), tris(dibenzylideneacetone)dipalladium (0) chloroform complex (13.0 mg, 0.013 mmol) and bis(tri-t-butylphosphine)palladium(0) (16.0 mg, 0.031 mmol) in tetrahydrofuran (2.0 mL) was heated to reflux for 15 h. The reaction mixture was cooled to room temperature, diluted with diethyl ether (100 mL), washed with saturated ammonium chloride solution and brine. The organic layer was separated, dried with sodium sulfate, filtered and concentrated. Purification by medium pressure liquid chromatography on silica gel (1:5 ethyl acetate/hexanes) gave 59 mg (81%) of the title compound as a semisolid. MS 571.2 (M+H)$^+$.

Step G: (S)-2-[5-Naphthalen-1-yl-2-oxo-3-(4-trifluoromethylbenzoylamino)-2H-pyridin-1-yl]-3-phenylpropionic acid A mixture of (S)-2-[5-naphthalen-1-yl-2-oxo-3-(4-trifluoromethyl-benzoylamino)-2H-pyridin-1-yl]-3-phenylpropionic acid methyl ester from Step F (31 mg, 0.054 mmol) and 1N lithium hydroxide (2.0 mL) in tetrahydrofuran (2.0 mL) was stirred at room temperature for 1 h. 1N Hydrochloric acid (3 mL) was added and the mixture was extracted with dichloromethane (3×10 mL). The combined organic layer was dried with sodium sulfate, filtered and concentrated in vacuo to give a quantitative yield of the title compound. MS 557.1 (M+H)$^+$.

Compound 2

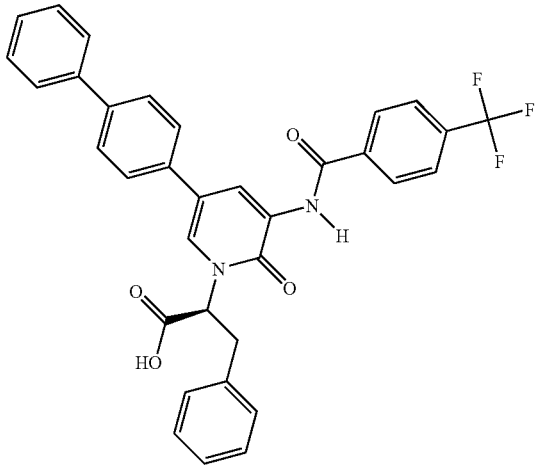

(S)-2-[5-Biphenyl-4-yl-2-oxo-3-(4-trifluoromethylbenzoylamino)-2H-pyridin-1-yl]-3-phenylpropionic acid The title compound was prepared by a procedure analogous to that of Compound 1 by substituting (1,1'-biphenyl-4-yl)boronic acid for 1-naphthyleneboronic acid of Step F in Compound 1. MS 583.0 (M+H)+.

The title compound was prepared by a procedure analogous to that of Compound 1 by substituting 4-phenoxyphenylboronic acid for 1-naphthyleneboronic acid of Step F in Compound 1. MS 599.1 (M+H)+.

Compound 3

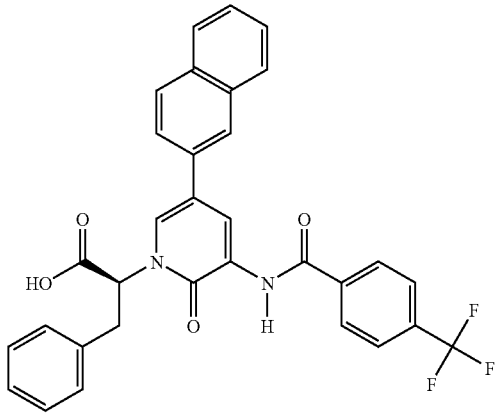

(S)-2-[5-Naphthalen-2-yl-2-oxo-3-(4-trifluoromethylbenzoylamino)-2H-pyridin-1-yl]-3-phenylpropionic acid The title compound was prepared by a procedure analogous to that of Compound 1 by substituting 2-naphthyleneboronic acid for 1-naphthyleneboronic acid of Step F in Compound 1. MS 557.1 (M+H)+.

Compound 5

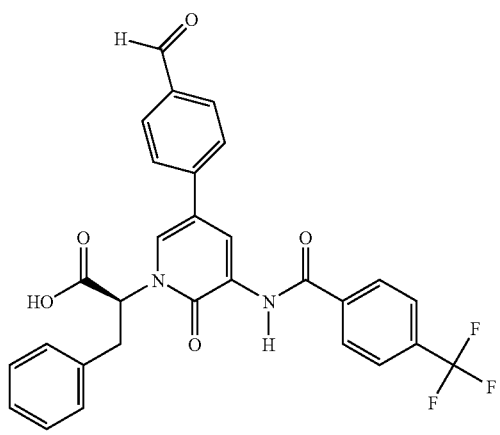

(S)-2-[5-(4-Formylphenyl)-2-oxo-3-(4-trifluoromethylbenzoylamino)-2H-pyridin-1-yl]-3-phenylpropionic acid The title compound was prepared by a procedure analogous to that of Compound 1 by substituting 4-formylphenylboronic acid for 1-naphthyleneboronic acid of Step F in Compound 1. MS 535.2 (M+H)+.

Compound 4

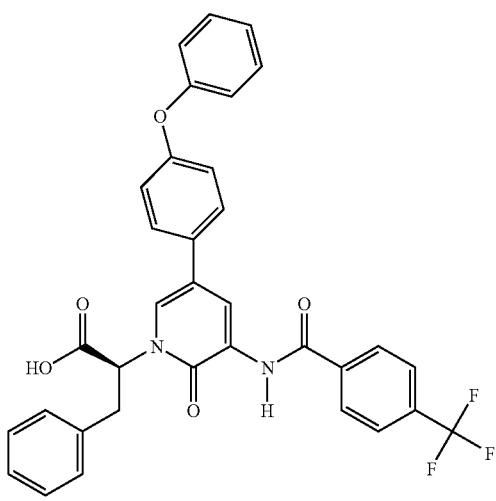

(S)-2-[2-Oxo-5-(4-phenoxyphenyl)-3-(4-trifluoromethylbenzoylamino)-2H-pyridin-1-yl]-3-phenylpropionic acid Compound 6

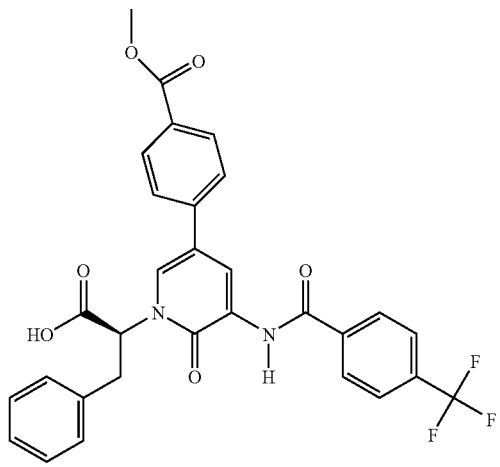

(S)-4-[1-(1-Carboxy-2-phenethyl)-6-oxo-5-(4-trifluoromethylbenzoylamino)-1,6-dihydro-pyridin-3-yl]benzoic acid methyl ester The title compound was prepared by a procedure analogous to that of Compound 1 by substituting (4-methoxycarbonylphenyl)boronic acid for 1-naphthyleneboronic acid of Step F in Compound 1. MS 565.2 (M+H)+.

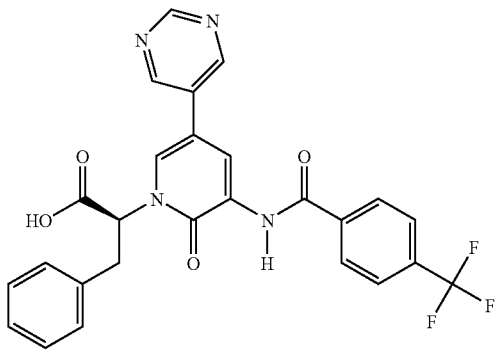

Compound 7

(S)-2-[2-Oxo-5-pyrimidin-5-yl-3-(4-trifluoromethyl-benzoylamino)-2H-pyridin-1-yl]-3-phenylpropionic acid The title compound was prepared by a procedure analogous to that of Compound 1 by substituting pyrimidine-5-boronic acid for 1-naphthyleneboronic acid of Step F in Compound 1. MS 531.3 (M+Na)$^+$.

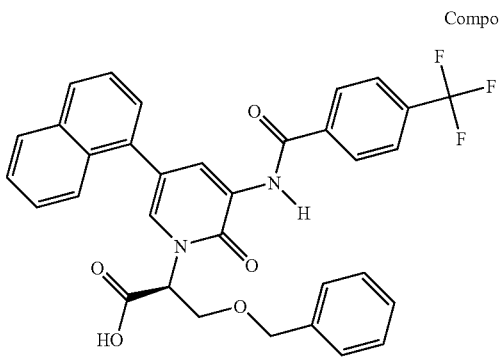

Compound 8

(S)-3-Benzyloxy-2-[5-naphthalen-1-yl-2-oxo-3-(4-trifluoromethylbenzoylamino)-2H-pyridin-1-yl]propionic acid Steps A-E: (S)-3-Benzyloxy-2-[5-bromo-2-oxo-3-(4-trifluoromethyl-benzoylamino)-2H-pyridin-1-yl] propionic acid methyl ester The intermediate (S)-3-benzyloxy-2-[5-bromo-2-oxo-3-(4-trifluoromethyl-benzoylamino)-2H-pyridin-1-yl]propionic acid methyl ester was prepared by a procedure analogous to that of Steps A-E of Compound 1, by substituting (R)-3-benzyloxy-2-hydroxypropionic acid (prepared from (R)-D-O-benzylserine by the procedure described in: A. Focella, F. Bizzarro, C. Exon *Synth. Commun.* 1991, 21, 2165) for 2-hydroxy-3-phenylpropionic acid of Step A in Compound 1.

Step F: (S)-3-Benzyloxy-2-[5-naphthalen-1-yl-2-oxo-3-(4-trifluoromethyl-benzoyl amino)-2H-pyridin-1-yl]propionic acid methyl ester A mixture of the 3-benzyloxy-2-[5-bromo-2-oxo-3-(4-trifluoromethyl-benzoylamino)-2H-pyridin-1-yl]propionic acid methyl ester from above (0.042 mmol), tetrakis(triphenylphosphine)palladium(0) (10 mg, 0.008 mmol) and sodium carbonate (9 mg, 0.083 mmol) in ethanol/water/dimethoxyethane (1:1:10 by volume, 2 mL) was stirred and heated at 150° C. for 5 min under microwave (CEM). The reaction mixture was cooled to room temperature, diluted with diethyl ether (50 mL), washed with saturated ammonium chloride solution and brine. The organic layer was separated, dried with sodium sulfate, filtered and concentrated. Purification by medium pressure liquid chromatography on silica gel (1:5 ethyl acetate/hexanes) gave the pyridone ester in 10-90% yield.

Step G: (S)-3-Benzyloxy-2-[5-naphthalen-1-yl-2-oxo-3-(4-trifluoromethyl-benzoylamino)-2H-pyridin-1-yl]propionic acid The title compound was obtained by a procedure analogous to that of Step G in Compound 1. MS 586.6 (M+H)$^+$.

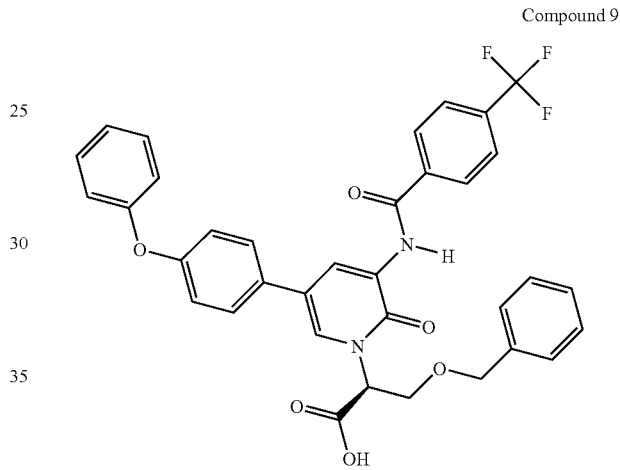

Compound 9

(S)-3-Benzyloxy-2-[2-oxo-5-(4-phenoxyphenyl)-3-(4-trifluoromethyl-benzoylamino)-2H-pyridin-1-yl]propionic acid The title compound was prepared by a procedure analogous to that of Compound 8 by substituting 4-phenoxyphenylboronic acid for 1-naphthyleneboronic acid of Step F in Compound 8. MS 629.1 (M+H)$^+$.

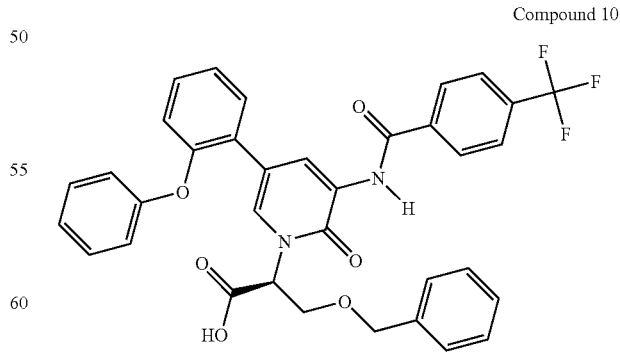

Compound 10

(S)-3-Benzyloxy-2-[2-oxo-5-(2-phenoxyphenyl)-3-(4-trifluoromethyl-benzoylamino)-2H-pyridin-1-yl] propionic acid The title compound was prepared by a procedure analogous to that of Compound 8 by substituting 2-phenoxyphenylboronic acid for 1-naphthyleneboronic acid of Step F in Compound 8. MS 629.1 (M+H)⁺.

Compound 11

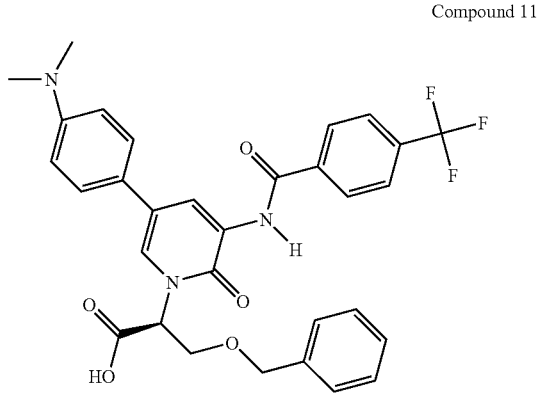

(S)-3-Benzyloxy-2-[5-(4-dimethylaminophenyl)-2-oxo-3-(4-trifluoromethyl-benzoylamino)-2H-pyridin-1-yl]propionic acid The title compound was prepared by a procedure analogous to that of Compound 8 by substituting (4-dimethylamino)phenylboronic acid for 1-naphthyleneboronic acid of Step F in Compound 8. MS 580.0 (M+H)⁺.

Compound 12

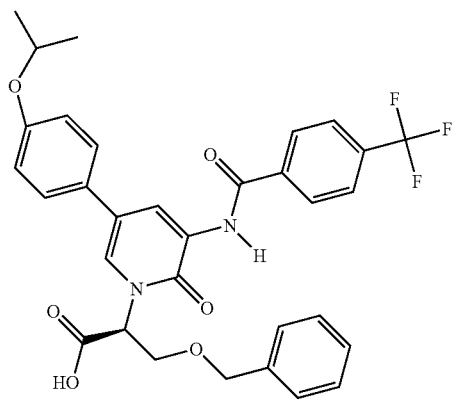

(S)-3-Benzyloxy-2-[5-(4-isopropoxyphenyl)-2-oxo-3-(4-trifluoromethyl-benzoylamino)-2H-pyridin-1-yl]propionic acid The title compound was prepared by a procedure analogous to that of Compound 8 by substituting (4-isopropoxy)phenylboronic acid for 1-naphthyleneboronic acid of Step F in Compound 8. MS 595.0 (M+H)⁺.

Compound 13

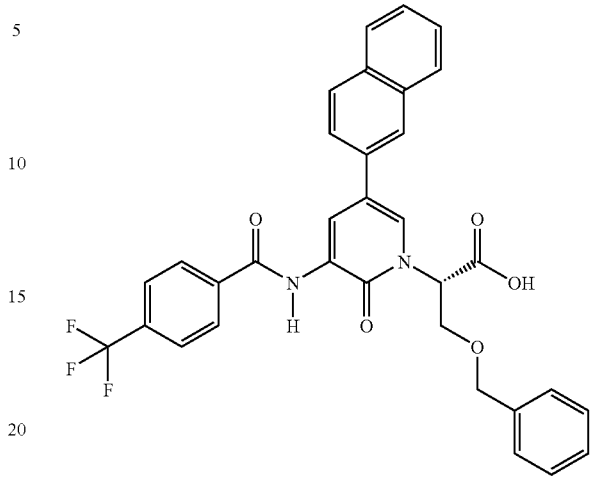

(S)-3-Benzyloxy-2-[5-naphthalen-2-yl-2-oxo-3-(4-trifluoromethylbenzoylamino)-2H-pyridin-1-yl]propionic acid The title compound was prepared by a procedure analogous to that of Compound 8 by substituting 2-naphthyleneboronic acid for 1-naphthyleneboronic acid of Step F in Compound 8. MS 585.2 (M−H)⁻¹.

Compound 14

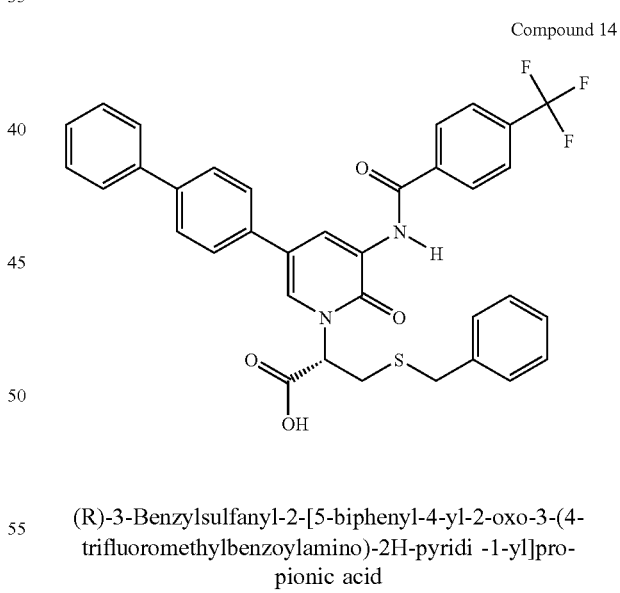

(R)-3-Benzylsulfanyl-2-[5-biphenyl-4-yl-2-oxo-3-(4-trifluoromethylbenzoylamino)-2H-pyridi -1-yl]propionic acid The title compound was prepared by a procedure analogous to that of Compound 8 by substituting (S)-3-benzylsulfanyl-2-hydroxypropionic acid (the preparation is in a similar manner to (R)-3-benzyloxy-2-hydroxypropionic acid) for (R)-3-benzyloxy-2-hydroxypropionic acid of Step A in Compound 8, and by substituting (1,1'-biphenyl-4-yl) boronic acid for 1-naphthyleneboronic acid of Step F in Compound 8. MS 627.0 (M−H)⁻.

Compound 15

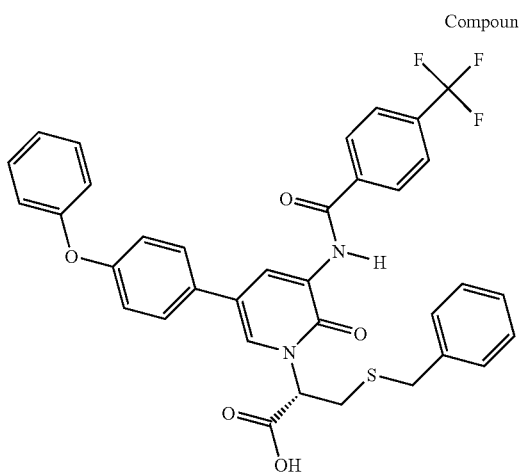

(R)-3-Benzylsulfanyl-2-[2-oxo-5-(4-phenoxyphenyl)-3-(4-trifluoromethyl-benzoylamino)-2H-pyridin-1-yl]propionic acid The title compound was prepared by a procedure analogous to that of Compound 8 by substituting (S)-3-benzylsulfanyl-2-hydroxypropionic acid for (R)-3-benzyloxy-2-hydroxypropionic acid of Step A in Compound 8, and by substituting 4-phenoxyphenylboronic acid for 1-naphthyleneboronic acid of Step F in Compound 8. MS 643.1 (M–H)⁻.

Compound 16

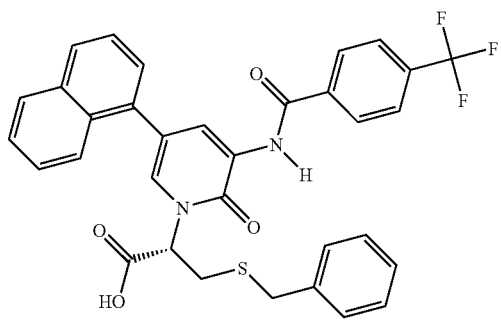

(R)-3-Benzylsulfanyl-2-[5-naphthalen-1-yl-2-oxo-3-(4-trifluoromethyl-benzoylamino)-2H-pyridin-1-yl]propionic acid The title compound was prepared by a procedure analogous to that of Compound 8 by substituting (S)-3-benzylsulfanyl-2-hydroxypropionic acid for (R)-3-benzyloxy-2-hydroxypropionic acid of Step A in Compound 8. MS 601.0 (M–H)⁻.

Compound 17

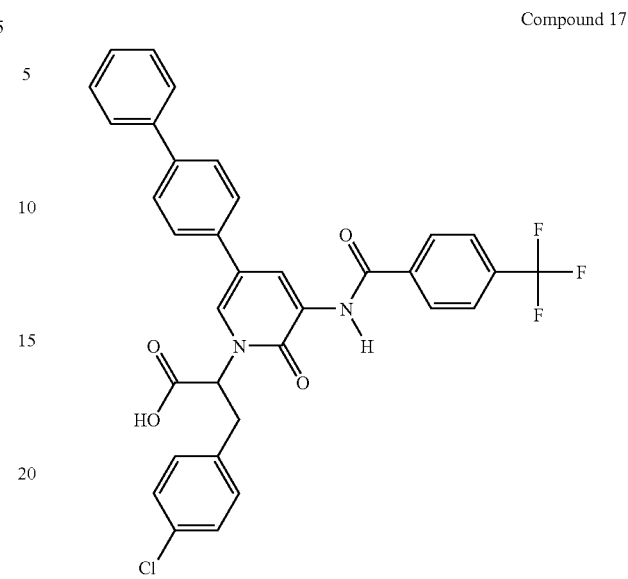

2-[5-Biphenyl-4-yl-2-oxo-3-(4-trifluoromethylbenzoylamino)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid (the preparation is in a similar manner to (R)-3-benzyloxy-2-hydroxypropionic acid) for (R)-3-benzyloxy-2-hydroxypropionic acid of Step A in Compound 8, and by substituting (1,1'-biphenyl-4-yl)boronic acid for 1-naphthyleneboronic acid of Step F in Compound 8. MS 616.0 (M–H)⁻

Compound 18

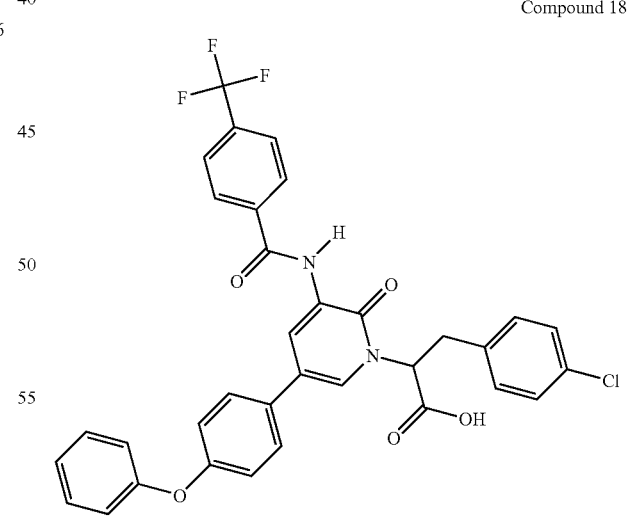

3-(4-Chlorophenyl)-2-[2-oxo-5-(4-phenoxyphenyl)-3-(4-trifluoromethyl-benzoylamino)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting 4-phenoxyphenylboronic acid for 1-naphthyleneboronic acid of Step F in Compound 8. MS 631.1 (M–H)⁻

Compound 19

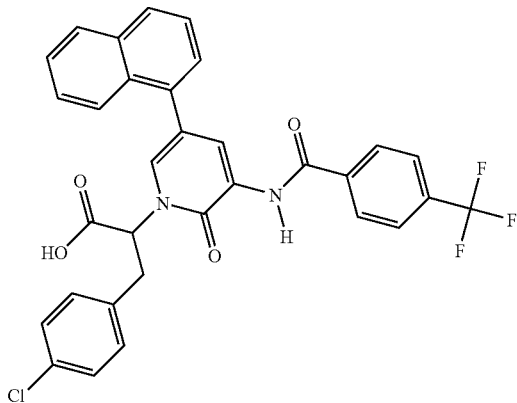

3-(4-Chlorophenyl)-2-[5-naphthalen-1-yl-2-oxo-3-(4-trifluoromethyl-benzoylamino)-2H -1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8. MS 591.0 (M+H)⁺

Compound 20

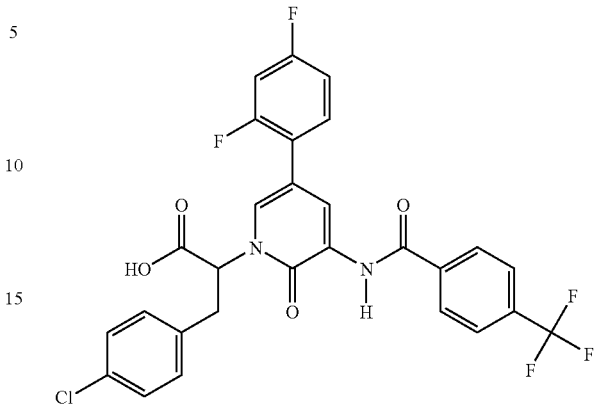

3-(4-Chlorophenyl)-2-[5-(3,4-dichloro-phenyl)-2-oxo-3-(4-trifluoromethyl-benzoylamino)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2hydroxypropionic acid of Step A in Compound 8, and by substituting 3,4-dichlorophenyl boronic acid for 1-naphthyleneboronic acid of Step F in Compound 8. MS 611.0 (M+H)⁺

Compound 21

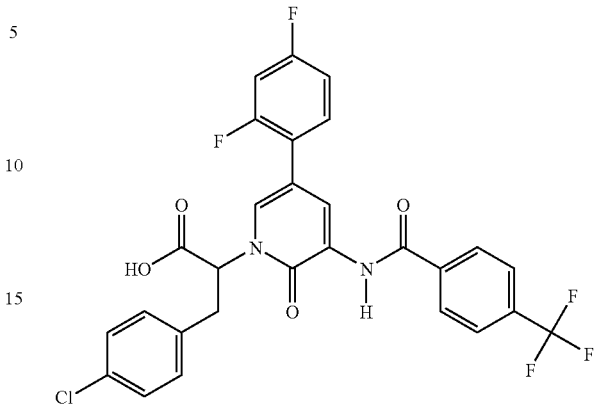

3-(4-Chlorophenyl)-2-[5-(2,4-difluorophenyl)-2-oxo-3-(4-trifluoromethyl-benzoylamino)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting 2,4-difluorophenyl boronic acid for 1-naphthyleneboronic acid of Step F in Compound 8. MS 577.0 (M+H)+

Compound 22

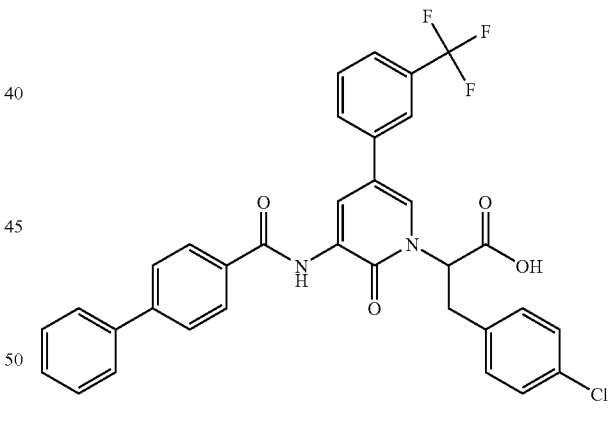

2-[3-[(Biphenyl-4-carbonyl)amino]-2-oxo-5-(3-trifluoromethylphenyl)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3-trifluoromethylphenyl boronic acid for 1-naphthyleneboronic acid of Step F in Compound 8. MS 616.0 (M–H)⁻

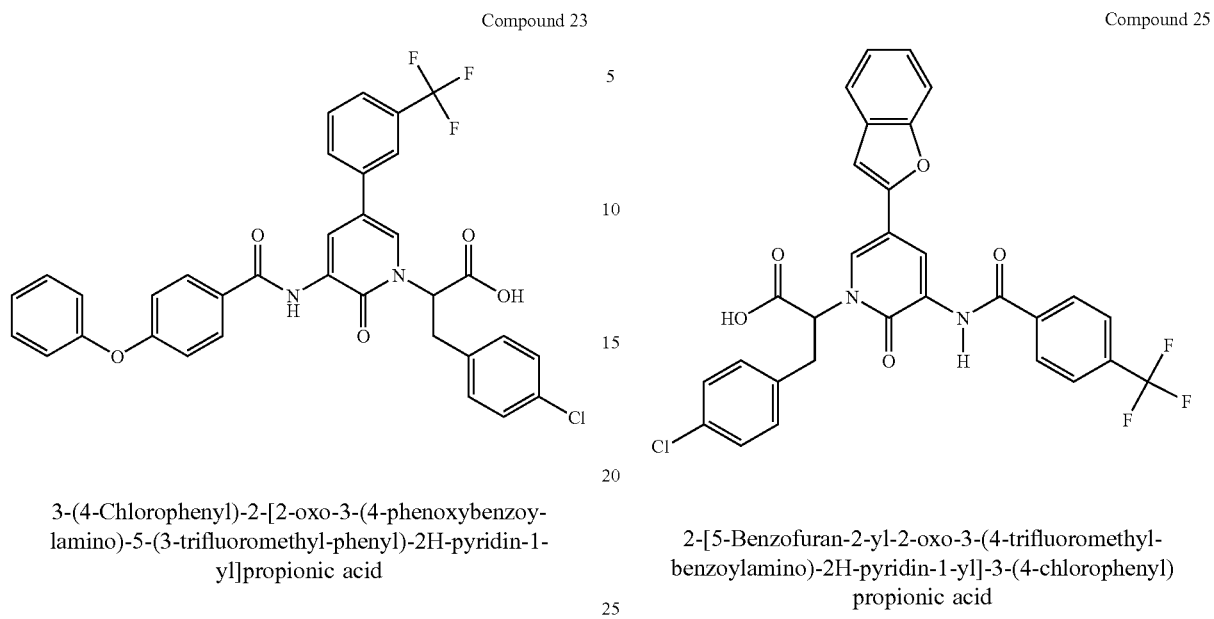

Compound 23

3-(4-Chlorophenyl)-2-[2-oxo-3-(4-phenoxybenzoy-lamino)-5-(3-trifluoromethyl-phenyl)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting 4-phenoxy-benzoyl chloride for 4-trifluoromethylbenzoyl chloride of step D in Compound 8, and by substituting 3-trifluoromethylphenylboronic acid for 1-naphthyleneboronic acid of Step F in Compound 8. MS 633.0 (M+H)+

Compound 25

2-[5-Benzofuran-2-yl-2-oxo-3-(4-trifluoromethyl-benzoylamino)-2H-pyridin-1-yl]-3-(4-chlorophenyl) propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting benzofuran-2-boronic acid for 1-naphthyleneboronic acid of Step F in Compound 8. MS 581.0 (M+H)+

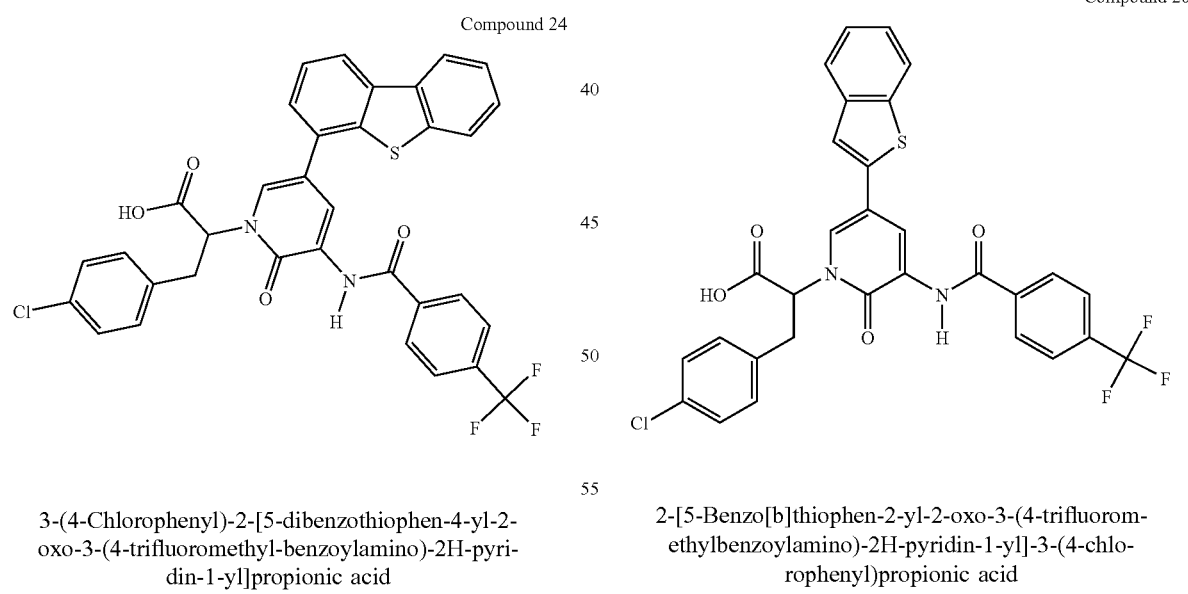

Compound 24

3-(4-Chlorophenyl)-2-[5-dibenzothiophen-4-yl-2-oxo-3-(4-trifluoromethyl-benzoylamino)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2hydroxypropionic acid of Step A in Compound 8, and by substituting dibenzothiophen-4-boronic acid for 1-naphthyleneboronic acid of Step F in Compound 8. MS 647.1 (M+H)+

Compound 26

2-[5-Benzo[b]thiophen-2-yl-2-oxo-3-(4-trifluoromethylbenzoylamino)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting benzo[b]thiophene-2-boronic acid for 1-naphthyleneboronic acid of Step F in Compound 8. MS 597.0 (M+H)+

Compound 27

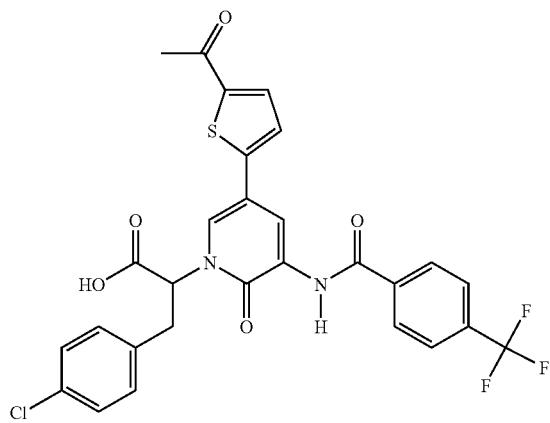

2-[5-(5-Acetylthiophen-2-yl)-2-oxo-3-(4-trifluorom-
ethylbenzoylamino)-2H-pyridin-1-yl]-3-(4-chlo-
rophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting 5-acetylthiophene-2-boronic acid for 1-naphthyleneboronic acid of Step F in Compound 8. MS 589.0 (M+H)$^+$ Compound 28

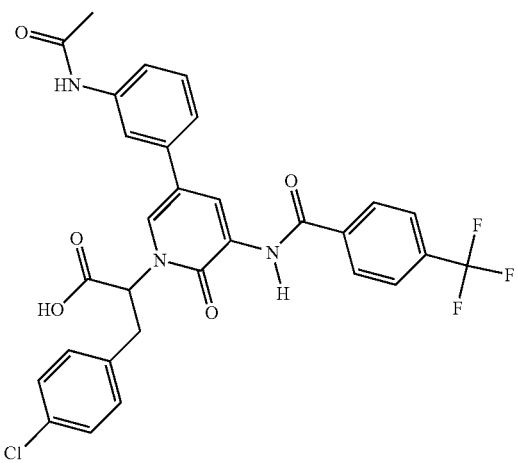

2-[5-(3-Acetylaminophenyl)-2-oxo-3-(4-trifluorom-
ethylbenzoylamino)-2H-pyridin-1-yl]-3-(4-chlo-
rophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting 3-acetyl-aminophenyl boronic acid for 1-naphthyleneboronic acid of Step F in Compound 8. MS 598.0 (M+H)$^+$ Compound 29

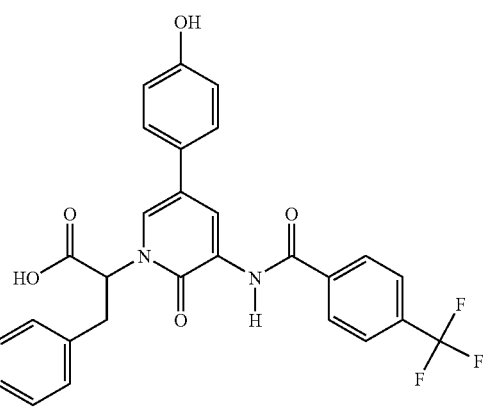

3-(4-Chlorophenyl)-2-[5-(4-hydroxyphenyl)-2-oxo-
3-(4-trifluoromethyl-benzoylamino)-2H-pyridin-1-
yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting 4-hydroxy-phenylboronic acid for 1-naphthyleneboronic acid of Step F in Compound 8. MS 557.0 (M+H)$^+$ Compound 30

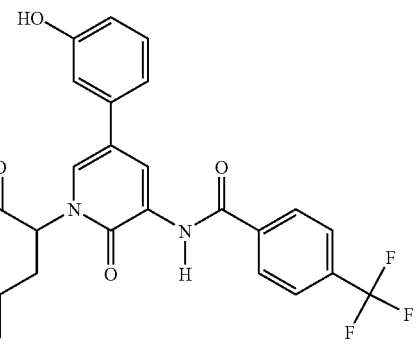

3-(4-Chlorophenyl)-2-[5-(3-hydroxyphenyl)-2-oxo-
3-(4-trifluoromethyl-benzoylamino)-2H-pyridin-1-
yl]propionic acid The title compound was prepared by a procedure analogous to that of Compound 8 by substituting 3-(4-chlorophenyl)-2-hydroxypropionic acid for (R)-3-benzyloxy-2hydroxypropionic acid of Step A in Compound 8, and by substituting 3-hydroxy-phenylboronic acid for 1-naphthyleneboronic acid of Step F in Compound 8. MS 557.1 (M+H)$^+$ Compound 31

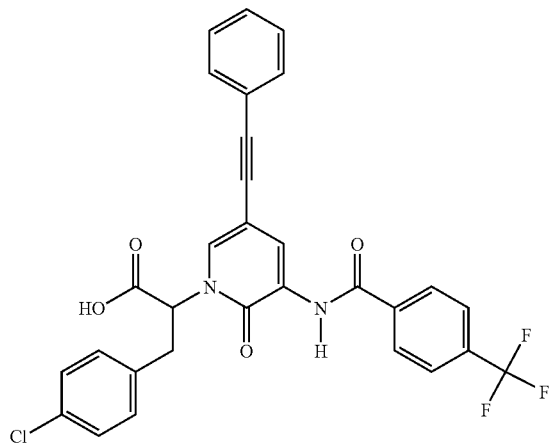

3-(4-Chlorophenyl)-2-[2-oxo-5-phenylethynyl-3-(4-trifluoromethylbenzoylamino)-2H-pyridin-1-yl]propionic acid

Steps A-E: 2-[5-bromo-2-oxo-3-(4-trifluoromethylbenzoylamino)-2H-pyridin-1-yl]-3-(4-chlorophenyl)propionic acid methyl ester The intermediate 2-[5-bromo-2-oxo-3-(4-trifluoromethylbenzoylamino)-2H-pyridin-1-yl]-3-(4-chlorophenyl)propionic acid methyl ester was prepared by a procedure analogous to that of Steps A-E of Compound 1, by substituting 3-(4-chlorophenyl)-2-hydroxypropionic acid for 2-hydroxy-3-phenylpropionic acid of Step A in Compound 1.

Step F: 3-(4-Chlorophenyl)-2-[2-oxo-5-phenylethynyl-3-(4-trifluoromethyl-benzoylamino)-2H-pyridin-1-yl]propionic acid methyl ester A mixture of 3-benzyloxy-2-[5-bromo-2-oxo-3-(4-trifluoromethyl-benzoylamino)-2H-pyridin-1-yl]propionic acid methyl ester from above (24 mg, 0.04 mmol), ethynylbenzene (22 mg, 0.21 mmol), tetrakis(triphenylphosphine)palladium(0) (10 mg, 0.008 mmol), copper iodide (2.0 mg, 0.008 mmol) and triethyl amine (1 mL) in N,N-dimethylformamide (1 mL) was stirred and heated under microwave (CEM) at 150° C. for 15 min. The reaction mixture was cooled to room temperature, diluted with diethyl ether (50 mL), washed with saturated ammonium chloride solution and brine. The organic layer was separated, dried with sodium sulfate, filtered and concentrated. Purification by medium pressure liquid chromatography on silica gel (1:5 ethyl acetate/hexanes) gave the pyridone ester 20 mg (82%) as a semisolid.

Step G: 3-Benzyloxy-2-[2-oxo-5-phenylethynyl-3-(4-trifluoromethyl benzoyl amino)-2H-pyridin-1-yl]propionic acid The title compound was obtained by a procedure analogous to that of Step G in Compound 1. MS 563.1 (M−H).

Compound 32

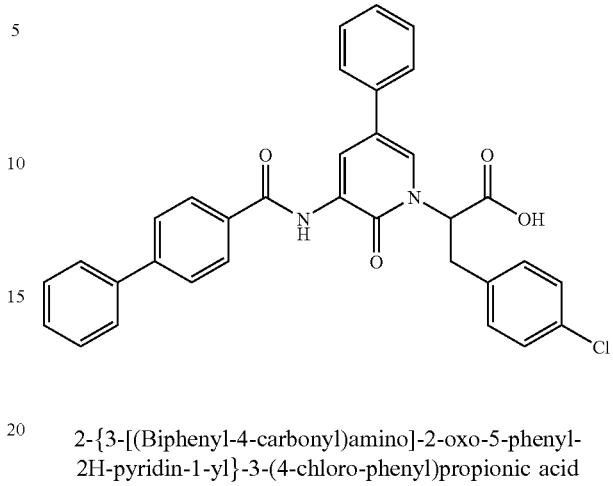

2-{3-[(Biphenyl-4-carbonyl)amino]-2-oxo-5-phenyl-2H-pyridin-1-yl}-3-(4-chloro-phenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting phenylboronic acid for 1-naphthyleneboronic acid of Step F in Compound 8. MS 549.2 (M+H)+

Compound 33

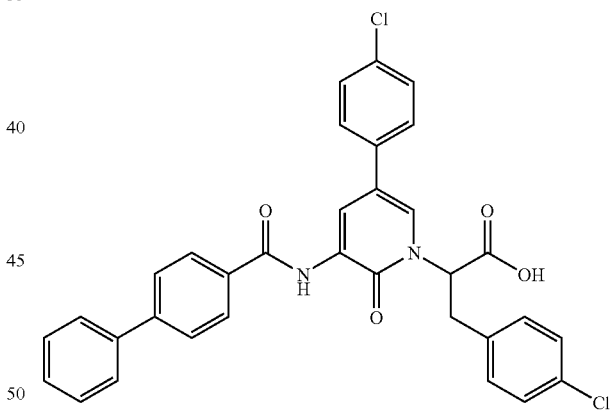

2-[3-[(Biphenyl-4-carbonyl)amino]-5-(4-chlorophenyl)-2-oxo-2H-pyridin-1-yl]-3(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-chlorophenyl boronic acid for 1-naphthyleneboronic acid of Step F in Compound 8. MS 581.1 (M−H)−

Compound 34

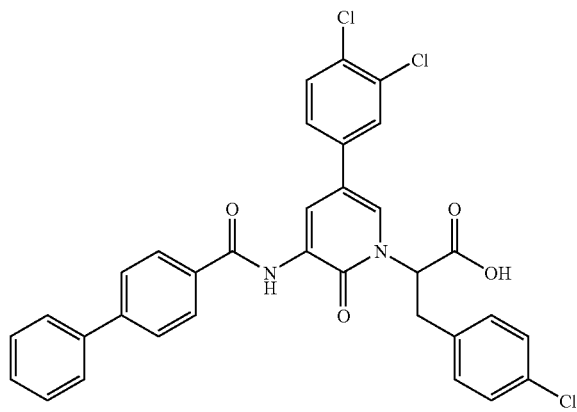

2-[3-[(Biphenyl-4-carbonyl)amino]-5-(3,4-dichlorophenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3,4-dichlorophenyl boronic acid for 1-naphthyleneboronic acid of Step F in Compound 8. MS 616.8 (M−H)⁻

Compound 36

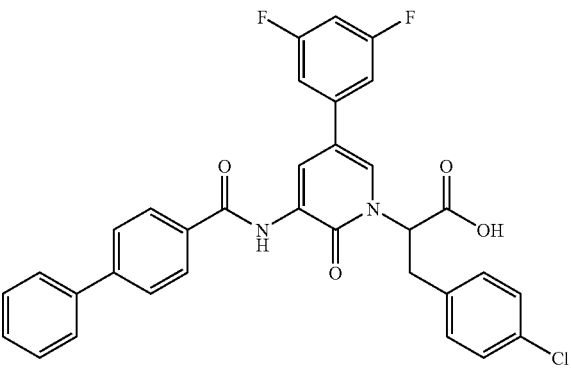

[3-[(Biphenyl-4-carbonyl)amino]-5-(3,5-difluorophenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3,5-difluorophenyl boronic acid for 1-naphthyleneboronic acid of Step F in Compound 8. MS 583.0 (M−H)⁻

Compound 35

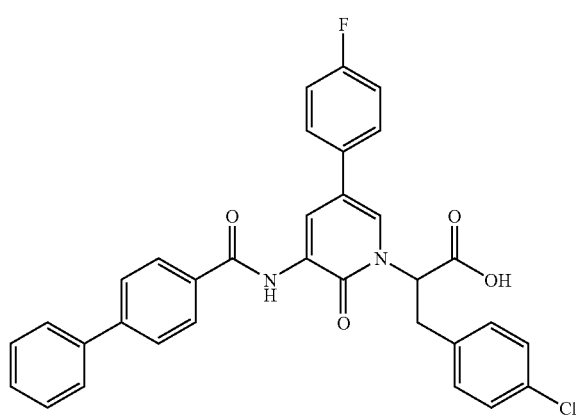

2-[3-[(Biphenyl-4-carbonyl)amino]-5-(4-fluorophenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-fluorophenylboronic acid for 1-naphthyleneboronic acid of Step F in Compound 8. MS 565.0 (M−H)⁻

Compound 37

2-[3-[(Biphenyl-4-carbonyl)amino]-5-(4-bromophenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-bromophenyl boronic acid for 1-naphthyleneboronic acid of Step F in Compound 8. MS 627.0 (M−H)⁻ substituting 4-hydroxyphenyl boronic acid for 1-naphthyleneboronic acid of Step F in Compound 8. MS 565.0 (M–H)⁻

Compound 38

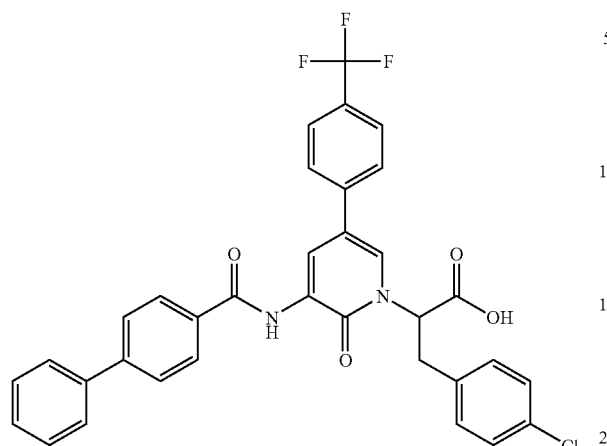

2-[3-[(Biphenyl-4-carbonyl)amino]-2-oxo-5-(4-trifluoromethylphenyl)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-trifluoromethylphenyl boronic acid for 1-naphthyleneboronic acid of Step F in Compound 8. MS 615.0 (M–H)⁻

Compound 39

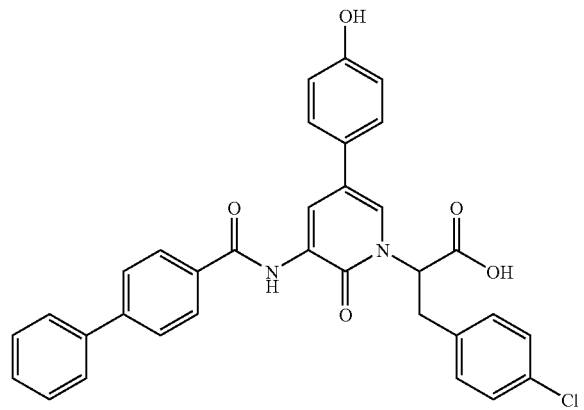

2-[3-[(Biphenyl-4-carbonyl)amino]-5-(4-hydroxyphenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by Compound 40

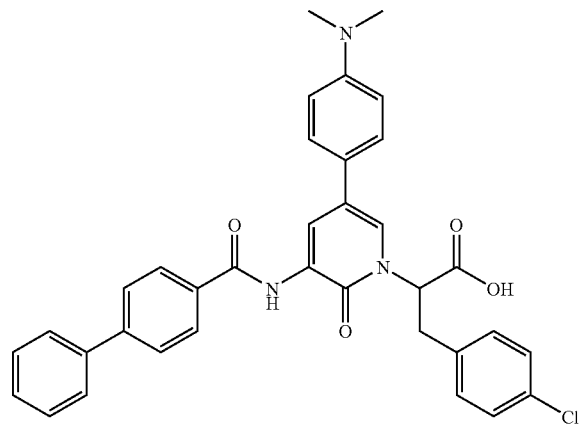

2-[3-[(Biphenyl-4-carbonyl)amino]-5-(4-dimethylaminophenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-dimethylaminophenyl boronic acid for 1-naphthyleneboronic acid of Step F in Compound 8. MS 590.1 (M–H)⁻

Compound 41

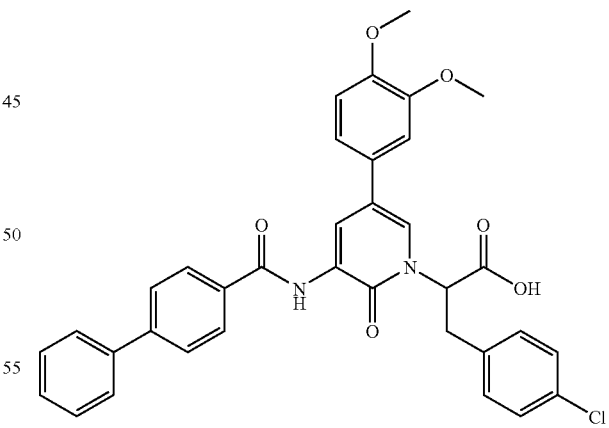

2-[3-[(Biphenyl-4-carbonyl)amino]-5-(3,4-dimethoxyphenyl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3,4-dimethoxyphenyl boronic acid for 1-naphthyleneboronic acid of Step F in Compound 8. MS 607.0 (M–H)⁻.

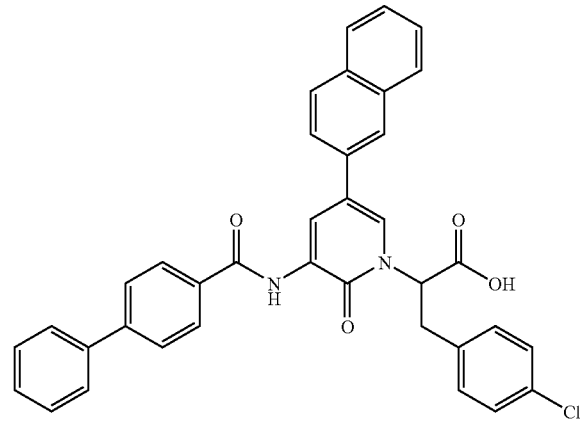

Compound 42

2-{3-[(Biphenyl-4-carbonyl)amino]-5-naphthalen-2-yl-2-oxo-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 2-naphthyleneboronic acid for 1-naphthyleneboronic acid of Step F in Compound 8. MS 598.0 (M–H)⁻.

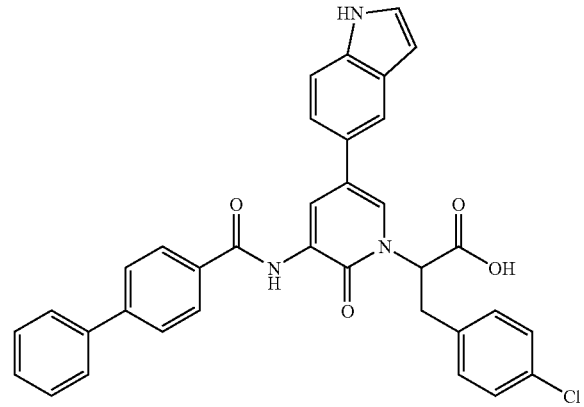

Compound 43

2-[3-[(Biphenyl-4-carbonyl)amino]-5-(1H-indol-5-yl)-2-oxo-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 1H-indole-5-boronic acid for 1-naphthyleneboronic acid of Step F in Compound 8. MS 586.0 (M–H)⁻.

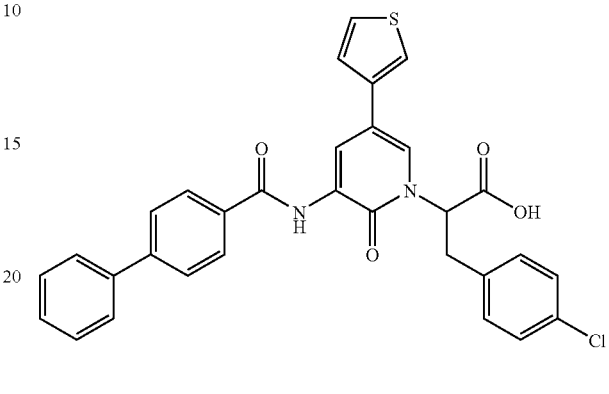

Compound 44

2-{3-[(Biphenyl-4-carbonyl)amino]-2-oxo-5-thiophen-3-yl-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3-thiophene boronic acid for 1-naphthyleneboronic acid of Step F in Compound 8. MS 553.0 (M–H)⁻.

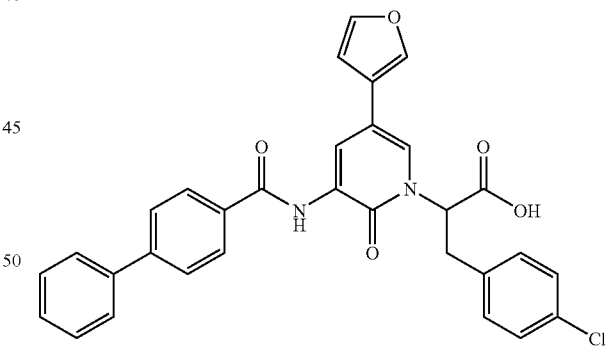

Compound 45

2-{3-[(Biphenyl-4-carbonyl)amino]-5-furan-3-yl-2-oxo-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 3-furan boronic acid for 1-naphthyleneboronic acid of Step F in Compound 8. MS 537.0 (M–H)⁻.

Compound 46

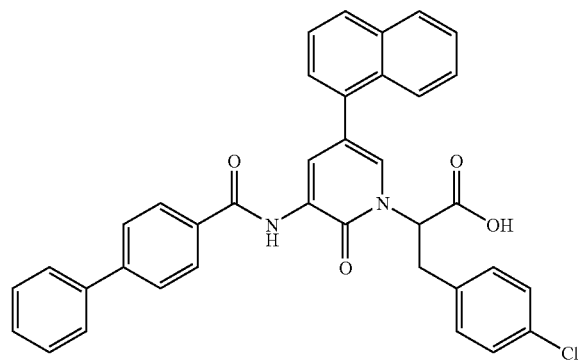

2-{3-[(Biphenyl-4-carbonyl)amino]-5-naphthalen-1-yl-2-oxo-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, and by substituting biphenyl-4-carbonyl chloride for 4-trifluoromethylbenzoyl chloride of step D in Compound 8. MS 599.2 (M−H)⁻.

Compound 47

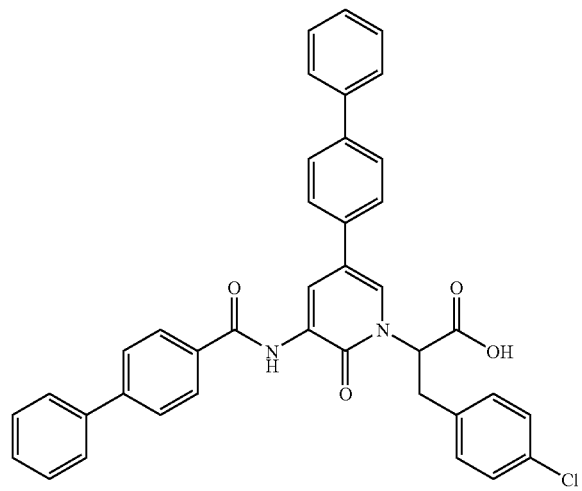

2-{3-[(Biphenyl-4-carbonyl)amino]-5-biphenyl-4-yl-2-oxo-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting (1,1'-biphenyl-4-yl)boronic acid for 1-naphthyleneboronic acid of Step F in Compound 8. MS 623.1 (M−H)⁻.

Compound 48

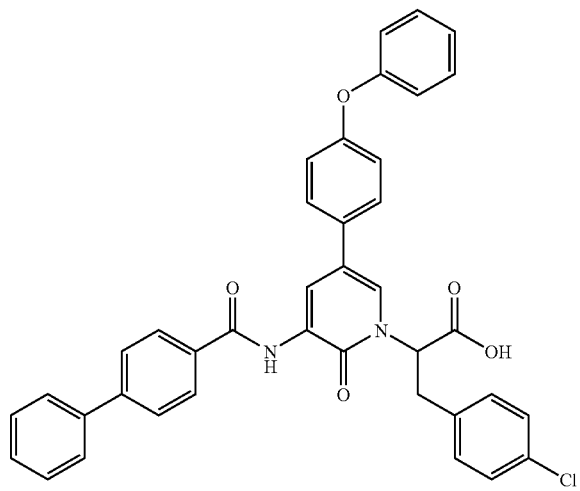

2-[3-[(Biphenyl-4-carbonyl)amino]-2-oxo-5-(4-phenoxyphenyl)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 4-phenoxyphenylboronic acid for 1-naphthyleneboronic acid of Step F in Compound 8. MS 641.0 (M−H)⁻.

Compound 49

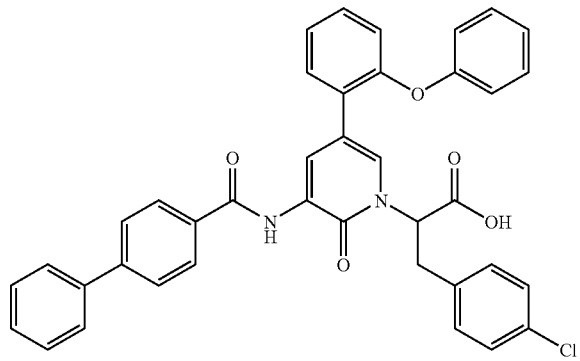

2-[3-[(Biphenyl-4-carbonyl)amino]-2-oxo-5-(2-phenoxyphenyl)-2H-pyridin-1-yl]-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride of step D in Compound 8, and by substituting 2-phenoxyphenylboronic acid for 1-naphthyl-eneboronic acid of Step F in Compound 8. MS 641.0 (M–H)⁻.

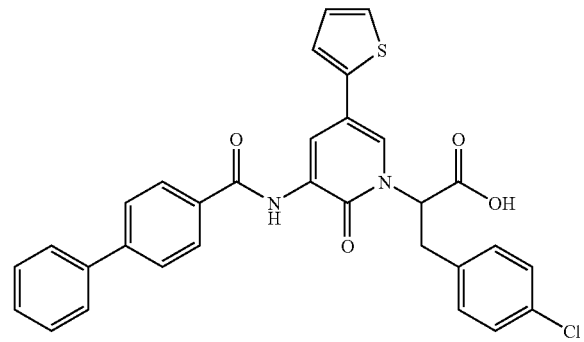

Compound 50

2-{3-[(Biphenyl-4-carbonyl)amino]-2-oxo-5-thiophen-2-yl-2H-pyridin-1-yl}-3-(4-chlorophenyl)propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting biphenyl-4-carbonyl chloride for 4-trifluoromethylbenzoyl chloride of step D in Compound 8, and by substituting 2-thiophene boronic acid for 1-naphthyleneboronic acid of Step F in Compound 8. $^1$HNMR δ (300 MHz, DMSO-$d_6$) 9.51 (1H, s), 8.27 (1H, d, J=9.9 Hz), 7.99 (2H, d, J=8.4 Hz), 7.83 (2H, d, J=8.4 Hz), 7.75 (2H, d, J=7.2 Hz), 7.66 (1H, d, J=7.2 Hz), 7.61–7.56 (2H, m), 7.59 (1H, s), 7.50 (1H, d, J=7.8 Hz), 7.43–7.41 (1H, m), 7.39–7.37 (1H, m), 7.33 (2H, d, J=8.4 Hz), 7.09 (2H, d, J=8.4 Hz), 5.40 (1H, t), 3.41 (2H buried d).

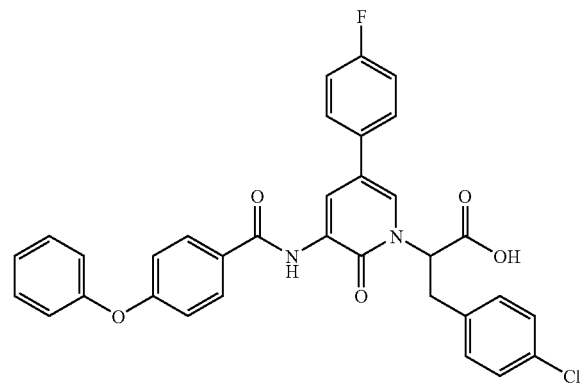

Compound 51

3-(4-Chlorophenyl)-2-[5-(4-fluorophenyl)-2-oxo-3-(4-phenoxybenzoylamino)-2H-pyridin 1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting 4-phenoxy-benzoyl chloride for 4-trifluoromethylbenzoyl chloride of step D in Compound 8, and by substituting 4-fluorophenylboronic acid for 1-naphthyleneboronic acid of Step F in Compound 8. MS 581.0 (M–H)⁻.

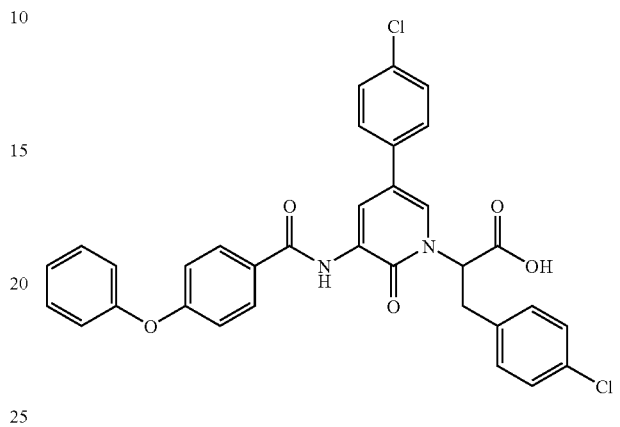

Compound 52

3-(4-Chlorophenyl)-2-[5-(4-chlorophenyl)-2-oxo-3-(4-phenoxybenzoylamino)-2H-pyridin 1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting 4-phenoxy-benzoyl chloride for 4-trifluoromethylbenzoyl chloride of step D in Compound 8, and by substituting 4-chlorophenyl boronic acid for 1-naphthyleneboronic acid of Step F in Compound 8. MS 599.1 (M–H)⁻.

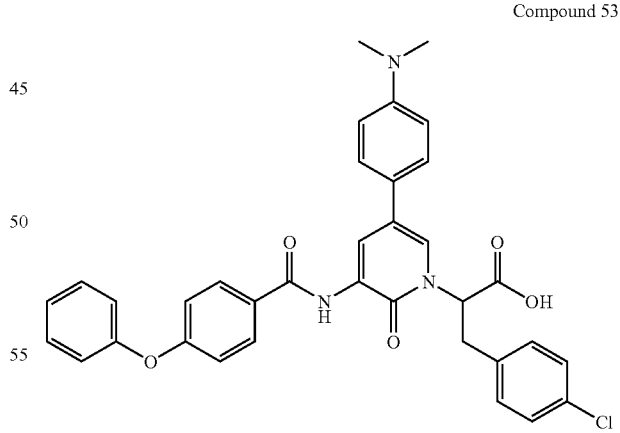

Compound 53

3-(4-Chlorophenyl)-2-[5-(4-dimethylaminophenyl)-2-oxo-3-(4-phenoxy-benzoylamino)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting 4-phenoxy-benzoyl chloride for 4-trifluoromethylbenzoyl chloride of step. D in Compound 8, and by substituting 4-dimethylaminophenyl boronic acid for 1-naphthyleneboronic acid of Step F in Compound 8. MS 606.2 (M–H)⁻.

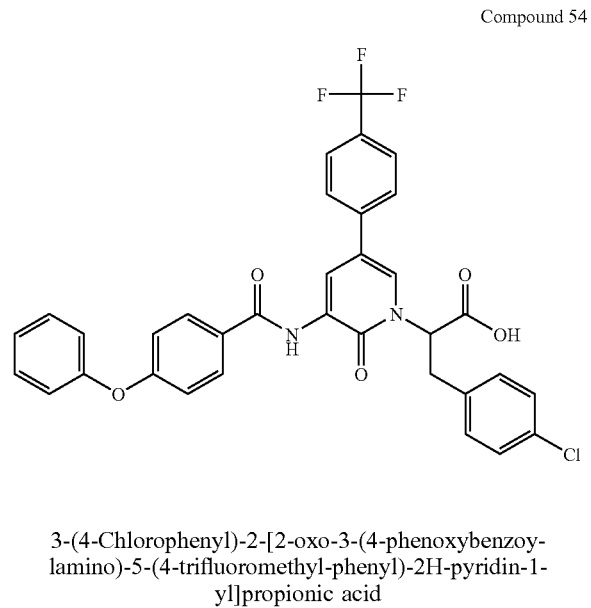

Compound 54

3-(4-Chlorophenyl)-2-[2-oxo-3-(4-phenoxybenzoylamino)-5-(4-trifluoromethyl-phenyl)-2H-pyridin-1-yl]propionic acid The title compound was prepared by a procedure analogous to that of Compound 8 by substituting 3-(4-chlorophenyl)-2-hydroxypropionic acid for (R)-3-benzyloxy-2-hydroxypropionic acid of Step A in Compound 8, by substituting 4-phenoxy-benzoyl chloride for 4-trifluoromethylbenzoyl chloride of step D in Compound 8, and by substituting 4-trifluoromethylphenyl boronic acid for 1-naphthyleneboronic acid of Step F in Compound 8. MS 632.0 (M–H)⁻.

Example 2

Assay to Evaluate Effect on Type III Protein Secretion Systems

The ability of the compounds of the invention to inhibit Type III protein secretion systems may be analyzed as follows.

Primary assay: Type III protein secretion of the chimeric SopÉ-Bla polypeptide by *Salmonella enterica*. This procedure is a cell-based assay that measures the type III-dependent secretion by *Salmonella enterica* of a plasmid-encoded chimeric polypeptide whose synthesis can be regulated, and which is endowed with an enzymatic activity that can be monitored calorimetrically by hydrolysis of a substrate that is unable to penetrate into the bacterial cytoplasm within the time constraints of the reaction. Thus, the colorimetric reaction is not influenced by SopÉ-Bla polypeptide in the bacterial cytoplasm. Instead, it effectively measures the amount of polypeptide that has been secreted from the *S. enterica* cytoplasm to the extracellular medium via type III system protein secretion.

The SopÉ-Bla recombinant polypeptide consists of two functionally distinct domains spliced together. The N-terminus domain is encoded by a polynucleotide region specifying the signal for type III secretion of the SopE polypeptide of *S. enterica*, an effector of the SPI1 type III protein secretion system. The C-terminus domain of SopÉ-Bla consists of a 263 amino acid peptide sequence that corresponds to the TEM-1 β-lactamase expressed by plasmid pBR322 but without its N-terminal signal sequence. The TEM-1 β-lactamase part of the SopÉ-Bla chimeric polypeptide is used as a reporter enzyme. It is capable of hydrolyzing nitrocefin resulting in a product whose accumulation can be monitored by colorimetric detection. The secretion of the SopÉ-Bla chimeric polypeptide from the cytoplasm to the extracellular medium is dependent on type III protein secretion.

For this procedure, cells grown under conditions known to favor a functional SPI1 secretion system are induced for expression of the SopÉ-Bla protein and grown either in the presence or in the absence of putative inhibitors for determined time. Nitrocefin is then added to the various cultures and its hydrolysis are used for quantitation. An inhibitor of Type III protein secretion is generally a compound that reduces the signal of the enzymatic reaction by decreasing the amount of SopÉ-Bla secreted into the extracellular medium.

Secondary assay: Type III-dependent protein secretion of the SipB polypeptide by *S. enterica*. The SipB protein of *S. enterica* is another effector of the SPI1 type III protein secretion system from *S. enterica*. In this cell-based procedure, the Type III-dependent secretion of SipB from the bacterial cytoplasm to the extracellular medium was measured through its reactivity with a cognate mouse monoclonal.

*Salmonella enterica* cells growing either in the presence or in the absence of inhibitors are induced for the production of SipB. Following an established period of growth the cells are sedimented and the amount of SipB present in the supernatant is quantified with a scanning imager following application of immunoblot techniques. Detection may employ an anti-SipB mouse monoclonal antibody (e.g., obtained from Jorge Galan, SUNY at Stony Brook, N.Y.) followed by treatment with commercially available sheep anti-mouse polyclonal antibody conjugated with horseradish peroxidase. Thereafter the membrane is treated with a peroxidase chemiluminescent substrate and exposed to film for an appropriate exposure time. Inhibition may be measured relative to untreated controls.

Tertiary assay: inhibition of Type III protein secretion of effectors from a *Pseudomonas aeruginosa* system. Type III protein secretion is used by *P. aeruginosa* to secrete several essential virulence determinants. One effector of the type III protein secretion system of *P. aeruginosa* PA103 is the virulence determinants ExoU.

The amount of Type III-dependent secretion of ExoU by *P. aeruginosa* PA103 can be determined in a cell-based assay by quantification of the 73.9 kDa ExoU protein secreted into the extracellular medium. Such quantitation can be achieved by growing strain PA103 in a deferrated medium in the presence of nitrilotriacetic acid (an inducer of Type III protein secretion in *P. aeruginosa*) and either in the presence or absence of putative inhibitors. After a prolonged growth period, the cells are sedimented and the supernatants concentrated by ammonium sulfate precipitation. The proteins in the resuspended pellets are separated by electrophoresis on SDS-polyacrylamide gels. After staining gels with Colloidal Blue™, the 73.9 kDa ExoU band is quantitated by scanning through an imager. The effects of inhibitors on the intensity of the ExoU band may be measured relative to that of untreated controls.

By way of example, assay results for preferred compounds of the invention are provided below in Table I.

TABLE I

| Compound | ExoU IC50(uM) | SipB IC50(uM) | SopE IC50(uM) |
|---|---|---|---|
| 1 | 82.80 | 82.80 | 14.40 |
| 2 |  | >100 | 9.30 |
| 3 |  | >100 | 28.50 |
| 4 | 84.70 | 84.70 | 6.30 |
| 5 | >100 | >100 | 49.90 |
| 6 | >100 | >100 | 53.60 |
| 7 |  | >100 | 82.30 |
| 8 | >100 | 49.20 | 29.50 |
| 9 | >100 | 26.20 | 10.10 |
| 10 | >100 | 37.40 | 27.00 |
| 11 |  | >100 | 76.00 |
| 12 |  | >100 | 67.20 |
| 13 |  | >100 | 48.00 |
| 14 | 31.60 | 7.10 | 31.30 |
| 15 | 83.40 | 67.90 | 9.10 |
| 16 |  | >100 | 6.40 |
| 17 |  | >100 | 2.00 |
| 18 |  | >100 | 2.30 |
| 19 |  | >100 | 5.50 |
| 20 | >100 | >100 | 2.70 |
| 21 | 61.20 | 79.00 | 13.50 |
| 22 | >100 | 38.30 | 3.40 |
| 23 |  | >100 | 9.80 |
| 24 | 62.40 | 67.10 | 1.60 |
| 25 |  | >100 | 3.70 |
| 26 |  | >100 | 2.40 |
| 27 |  | >100 | 34.20 |
| 28 |  | >100 | 52.40 |
| 29 |  | >100 | 31.80 |
| 30 | >100 | 33.40 | 19.30 |
| 31 |  | >100 | 34.20 |
| 32 |  | >100 | 2.30 |
| 33 | >50 | 39.00 | 7.60 |
| 34 | >100 | 24.80 | 8.70 |
| 35 | 7.50 | 58.40 | 2.30 |
| 36 |  | >100 | 2.40 |
| 37 |  | >100 | 1.50 |
| 38 | 21.30 | 3.10 | 1.20 |
| 39 | 80.50 | >100 | 3.60 |
| 40 | 56.40 | 10.20 | 2.80 |
| 41 | 67.40 | 15.90 | 3.20 |
| 42 | 41.30 | 76.20 | 1.10 |
| 43 | 28.00 | >100 | 1.90 |
| 44 | >100 | >100 | 2.80 |
| 45 | 49.40 | >100 | 4.00 |
| 46 |  | >100 | 1.10 |
| 47 | 39.40 | 55.00 | 1.40 |
| 48 | 33.20 | 35.00 | 1.20 |
| 49 | 46.30 | 48.00 | <0.8 |
| 50 | 51.40 | 27.00 | 6.40 |
| 51 | >100 | >100 | 4.90 |
| 52 |  | >100 | 9.00 |
| 53 | 49.00 | >100 | 3.60 |
| 54 |  | >100 | 16.60 |

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

REFERENCES

1. Preparation of N-[(oxypyridinylacetamido)alkoxy] guanidines and Analogs as Protease Inhibitors. Lu, T.; Tomczuk, B. E.; Markotan, T. P.; Siedem, C. WO 99/26926.

2. Preparation of Pyridonylacetamide Peptide Analogs as Antipicomaviral Agents. Dragovich, P. S.; Prins, T. J.; Zhou, R.; Johnson, T. O. WO 01/40189.

3. Preparation of Peptides as Selective Factor Xa Inhibitors. Zhu, B-Y.; Scarborough, R. M. WO 98/16547.

4. Peptidic Tetrazole Compounds having Interleukin-lb Converting Enzyme Inhibitory Activity. Kazuyuki, O.; Makoto, T.; Tohru, M.; Hiroyuki, O. EP 761680.

5. Structure-based Design, Synthesis and Biological Evaluation of Irreversible Human Rhinovirus 3C Protease Inhibitors. 6. Structure-activity Study of Orally Bioavailable, 2-Pyrimidone-containing Peptidomimetics. Dragovich, P. S.; Prins, T. J.; Zhou, R.; Brown, E. L.; Maldonado, F. C.; Fuhrman, S. A.; Zalman, L. S.; Tuntland, T.; Lee, C. A.; Patick, A. K.; Matthews, D. A.; Hendrickson, T. F.; Kosa, M. B.; Liu, B.; Batugo, M. R.; Gleeson, J-P. R.; Sakata, S. K.; Chen, L.; Guzman, M. C.; Meador, III, J. W.; Ferre, R. A.; and Worland, S. T. *J. Med. Chem.* 2002, 45, 1607.

What is claimed:

1. A compound of formula I:

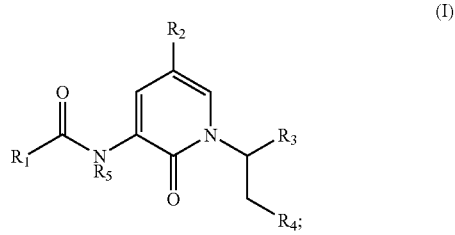

(I)

wherein $R_1$ is aryl, or substituted aryl;

$R_2$ is aryl-($C_2$–$C_4$ alkynyl)-; aryl, substituted aryl, or heteroaryl optionally substituted by acyl;

$R_3$ is hydrogen or carboxy;

$R_4$ is aryl, substituted aryl, benzylthio, or benzyloxy;

$R_5$ is hydrogen or lower alkyl;

or an optical isomer, diastereomer or enantiomer thereof; or a pharmaceutically acceptable salt, hydrate, ester or prodrug thereof.

2. The compound of claim 1 wherein $R_1$ is trifluoromethylphenyl, biphenyl, or phenoxyphenyl.

3. The compound of claim 1 wherein $R_2$ is naphthyl, phenoxyphenyl, or biphenyl.

4. The compound of claim 1 wherein $R_2$ is pyrimidinyl, furyl, thienyl, indolyl, dibenzothienyl, benzofuranyl, or benzothienyl.

5. The compound of claim 1 wherein $R_4$ is benzyloxy, benzylthio or chlorophenyl.

6. A compound of claim 1 having the formula:

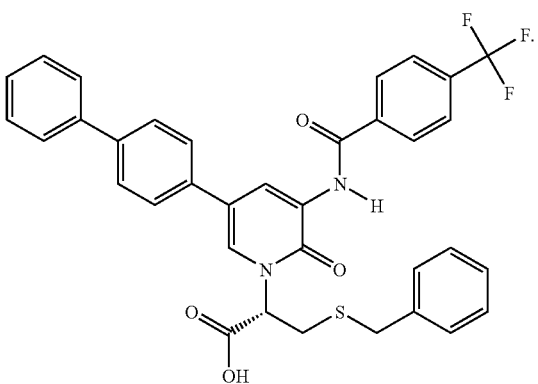

7. A compound of claim 1 having the Formula:

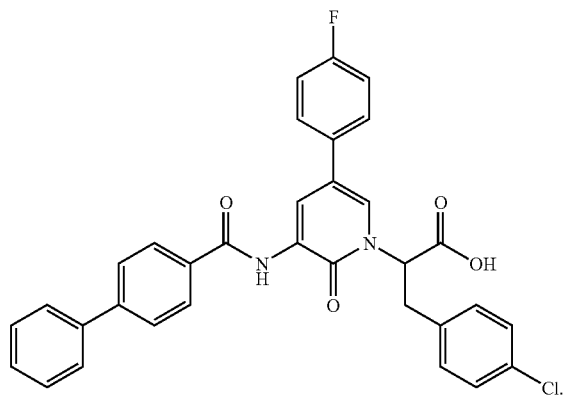

8. A compound of claim 1 having the Formula:

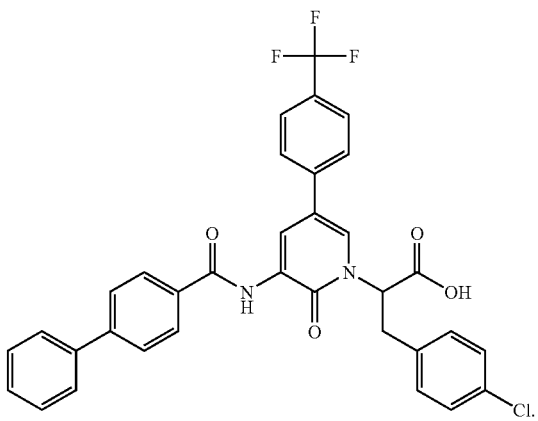

9. A compound of claim 1 having the Formula:

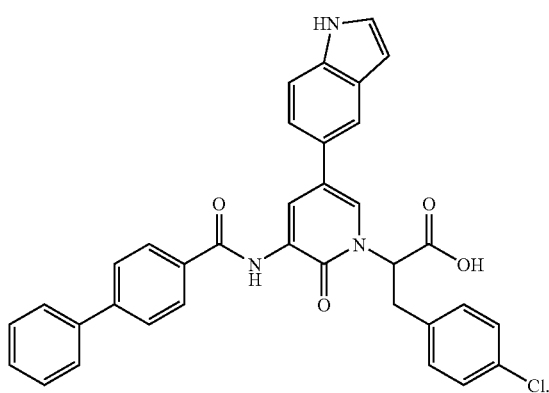

10. A compound of claim 1 having the Formula:

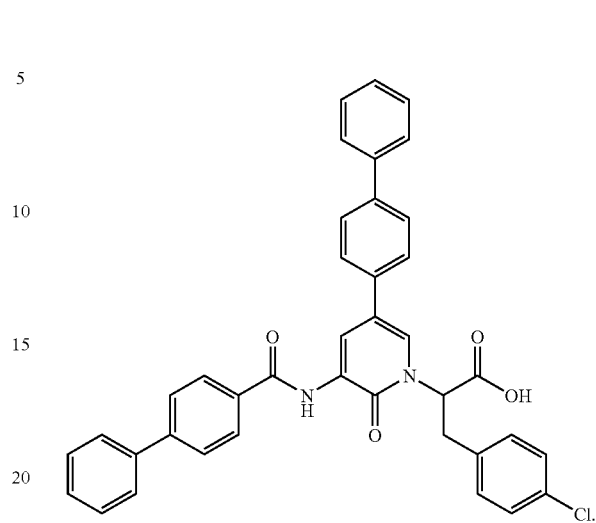

11. A compound of claim 1 having the Formula:

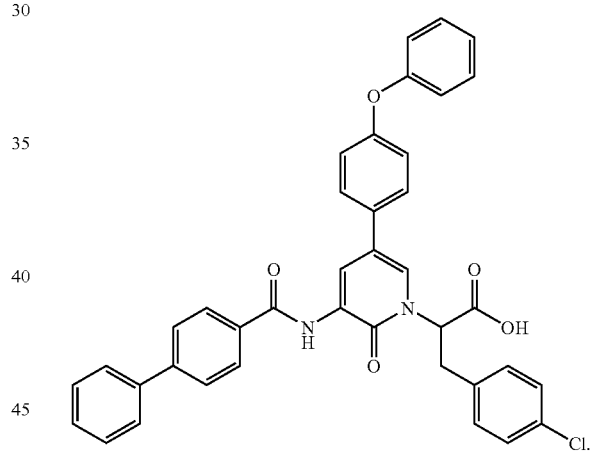

12. A method of inhibiting bacteria with Type III protein secretion systems, said method comprising administration of an effective amount of a compound according to claim 1 to a subject in need of treatment for infection by bacteria with said Type III protein secretion systems.

* * * * *